(12) United States Patent
Castro et al.

(10) Patent No.: US 9,675,380 B2
(45) Date of Patent: Jun. 13, 2017

(54) SURGICAL TOOL POSITIONING SYSTEM

(71) Applicants: Michael Salvatore Castro, Plymouth, MA (US); Christopher P. DeGeorge, Franklin, MA (US); J. Christopher Flaherty, Auburndale, FL (US); R. Maxwell Flaherty, Auburndale, FL (US); Arnold Oyola, Northborough, MA (US); Joseph A. Stand, III, Holden, MA (US); Samuel F. Straface, Duxbury, MA (US)

(72) Inventors: Michael Salvatore Castro, Plymouth, MA (US); Christopher P. DeGeorge, Franklin, MA (US); J. Christopher Flaherty, Auburndale, FL (US); R. Maxwell Flaherty, Auburndale, FL (US); Arnold Oyola, Northborough, MA (US); Joseph A. Stand, III, Holden, MA (US); Samuel F. Straface, Duxbury, MA (US)

(73) Assignee: Medrobotics Corporation, Raynham, MA (US)

( * ) Notice: Subject to any disclaimer, the term of this patent is extended or adjusted under 35 U.S.C. 154(b) by 187 days.

(21) Appl. No.: 14/418,993

(22) PCT Filed: Aug. 9, 2013

(86) PCT No.: PCT/US2013/054326
§ 371 (c)(1),
(2) Date: Feb. 2, 2015

(87) PCT Pub. No.: WO2014/026104
PCT Pub. Date: Feb. 13, 2014

(65) Prior Publication Data
US 2015/0282835 A1  Oct. 8, 2015

Related U.S. Application Data

(60) Provisional application No. 61/681,340, filed on Aug. 9, 2012, provisional application No. 61/751,498, filed
(Continued)

(51) Int. Cl.
*A61B 17/34* (2006.01)
*A61B 90/50* (2016.01)
(Continued)

(52) U.S. Cl.
CPC ...... *A61B 17/3423* (2013.01); *A61B 17/3403* (2013.01); *A61B 90/50* (2016.02);
(Continued)

(58) Field of Classification Search
CPC . A61B 17/3423; A61B 17/3403; A61B 90/50; A61B 90/90; A61B 2017/2906; A61B 2017/3407
(Continued)

(56) References Cited

U.S. PATENT DOCUMENTS 3,060,972 A  10/1962  Sheldon
3,557,780 A  1/1971  Sato
(Continued)

FOREIGN PATENT DOCUMENTS

DE  102010020220  11/2011
EP  0653922  11/2005
(Continued)

OTHER PUBLICATIONS

Extended European Search Report dated Jun. 1, 2016 issued in corresponding European Application No. 13827617.5-1659.
(Continued)

*Primary Examiner* — Pedro Philogene
*Assistant Examiner* — David C Comstock

(74) *Attorney, Agent, or Firm* — Onello & Mello, LLP

(57) ABSTRACT

Described is a tool positioning system comprising an introduction device, a first tool support and a second tool support. The introduction device is constructed and arranged to slidingly receive an articulating probe. The first tool support comprises at least one guide element constructed and arranged to slidingly receive a first tool. The first tool support is oriented toward a first operator location. The second tool support comprises at least one guide element constructed and arranged to slidingly receive a second tool. The second tool support is oriented toward a second operator location.

52 Claims, 8 Drawing Sheets

Related U.S. Application Data on Jan. 11, 2013, provisional application No. 61/825,297, filed on May 20, 2013, provisional application No. 61/818,878, filed on May 2, 2013.

(51) Int. Cl.
*A61B 17/29* (2006.01)
*A61B 90/11* (2016.01)

(52) U.S. Cl.
CPC ....... *A61B 90/11* (2016.02); *A61B 2017/2906* (2013.01); *A61B 2017/3407* (2013.01)

(58) Field of Classification Search
USPC ...................................................... 600/204
See application file for complete search history.

(56) References Cited

U.S. PATENT DOCUMENTS

| | | |
|---|---|---|
| 3,572,325 A | 3/1971 | Bazell et al. |
| 3,583,393 A | 6/1971 | Takahashi |
| 3,625,200 A | 12/1971 | Muller |
| 3,638,973 A | 2/1972 | Poletti |
| 3,703,968 A | 11/1972 | Uhrich et al. |
| 3,739,770 A | 6/1973 | Mori |
| 3,790,002 A | 2/1974 | Germond et al. |
| 3,892,228 A | 7/1975 | Mitsui |
| 3,920,972 A | 11/1975 | Corwin, Jr. et al. |
| 4,078,670 A | 3/1978 | Francois et al. |
| 4,108,211 A | 8/1978 | Tanaka |
| 4,150,329 A | 4/1979 | Dahlstrom |
| 4,221,997 A | 9/1980 | Flemming |
| 4,259,876 A | 4/1981 | Belyanin et al. |
| 4,260,319 A | 4/1981 | Motoda et al. |
| 4,299,533 A | 11/1981 | Ohnaka |
| 4,351,323 A | 9/1982 | Ouchi et al. |
| 4,432,349 A | 2/1984 | Oshiro |
| 4,445,184 A | 4/1984 | Noguchi |
| 4,474,174 A | 10/1984 | Petruzzi |
| 4,475,375 A | 10/1984 | Hill |
| 4,494,417 A | 1/1985 | Larson et al. |
| 4,496,278 A | 1/1985 | Kaise |
| 4,502,830 A | 3/1985 | Inaba et al. |
| 4,517,963 A | 5/1985 | Michel |
| 4,531,885 A | 7/1985 | Molaug |
| 4,535,207 A | 8/1985 | Lindqvist |
| 4,564,179 A | 1/1986 | Hollingsworth |
| 4,600,355 A | 7/1986 | Johnson |
| 4,655,257 A | 4/1987 | Iwashita |
| 4,661,032 A | 4/1987 | Arai |
| 4,666,366 A | 5/1987 | Davis |
| 4,700,693 A | 10/1987 | Lia et al. |
| 4,706,001 A | 11/1987 | Nakashima et al. |
| 4,726,355 A | 2/1988 | Okada |
| 4,780,045 A | 10/1988 | Akeel et al. |
| 4,787,369 A | 11/1988 | Allred, III et al. |
| 4,790,294 A | 12/1988 | Allred, III et al. |
| 4,796,607 A | 1/1989 | Allred, III et al. |
| 4,804,897 A | 2/1989 | Gordon et al. |
| 4,805,477 A | 2/1989 | Akeel |
| 4,806,066 A | 2/1989 | Rhodes et al. |
| 4,830,569 A | 5/1989 | Jannborg |
| 4,831,547 A | 5/1989 | Ishiguro et al. |
| 4,838,859 A | 6/1989 | Strassmann |
| 4,863,133 A | 9/1989 | Bonnell |
| 4,864,888 A | 9/1989 | Iwata |
| 4,873,965 A | 10/1989 | Danieli |
| 4,888,708 A | 12/1989 | Brantmark et al. |
| 4,900,218 A | 2/1990 | Sutherland |
| 4,941,457 A | 7/1990 | Hasegawa |
| 4,943,296 A | 7/1990 | Funakubo et al. |
| 4,947,827 A | 8/1990 | Opie et al. |
| 4,949,927 A | 8/1990 | Madocks et al. |
| 4,950,116 A | 8/1990 | Nishida |
| 4,956,790 A | 9/1990 | Tsuchihashi et al. |
| 4,979,949 A | 12/1990 | Matsen, III et al. |
| 4,998,916 A | 3/1991 | Hammerslag et al. |
| 5,005,558 A | 4/1991 | Aomori |
| 5,006,035 A | 4/1991 | Nakashima et al. |
| 5,012,169 A | 4/1991 | Ono et al. |
| 5,037,391 A | 8/1991 | Hammerslag et al. |
| 5,044,063 A | 9/1991 | Voellmer |
| 5,046,375 A | 9/1991 | Salisbury, Jr. et al. |
| 5,064,340 A | 11/1991 | Genov et al. |
| 5,078,140 A | 1/1992 | Kwoh |
| 5,086,401 A | 2/1992 | Glassman et al. |
| 5,105,819 A | 4/1992 | Wollschlager et al. |
| 5,108,368 A | 4/1992 | Hammerslag et al. |
| 5,143,475 A | 9/1992 | Chikama |
| 5,167,221 A | 12/1992 | Chikama |
| 5,174,277 A | 12/1992 | Matsumaru |
| 5,176,126 A | 1/1993 | Chikama |
| 5,178,129 A | 1/1993 | Chikama et al. |
| 5,179,935 A | 1/1993 | Miyagi |
| 5,193,963 A | 3/1993 | McAffee et al. |
| 5,195,968 A | 3/1993 | Lundquist et al. |
| 5,200,679 A | 4/1993 | Graham |
| 5,201,325 A | 4/1993 | McEwen et al. |
| 5,203,380 A | 4/1993 | Chikama |
| 5,203,772 A | 4/1993 | Hammerslag et al. |
| 5,217,003 A | 6/1993 | Wilk |
| 5,217,453 A | 6/1993 | Wilk |
| 5,236,432 A | 8/1993 | Matsen, III et al. |
| 5,251,611 A | 10/1993 | Zehel et al. |
| 5,254,088 A | 10/1993 | Lundquist et al. |
| 5,257,669 A | 11/1993 | Kerley et al. |
| 5,266,875 A | 11/1993 | Slotine et al. |
| 5,271,381 A | 12/1993 | Ailinger et al. |
| 5,297,443 A | 3/1994 | Wentz |
| 5,318,526 A | 6/1994 | Cohen |
| 5,327,905 A | 7/1994 | Avitall |
| 5,337,732 A | 8/1994 | Grundfest et al. |
| 5,386,741 A | 2/1995 | Rennex |
| 5,448,989 A | 9/1995 | Heckele |
| 5,524,180 A | 6/1996 | Wang et al. |
| 5,815,640 A | 9/1998 | Wang et al. |
| 5,841,950 A | 11/1998 | Wang et al. |
| 5,907,664 A | 5/1999 | Wang et al. |
| 6,080,181 A | 6/2000 | Jensen et al. |
| 6,132,368 A | 10/2000 | Cooper |
| 6,346,072 B1 | 2/2002 | Cooper |
| 6,837,846 B2 | 1/2005 | Jaffe et al. |
| 6,837,847 B2 | 1/2005 | Ewers et al. |
| 7,357,774 B2 | 4/2008 | Cooper |
| 7,789,875 B2 | 9/2010 | Brock et al. |
| 7,819,885 B2 | 10/2010 | Cooper |
| 7,850,642 B2 | 12/2010 | Moll et al. |
| 7,854,738 B2 | 12/2010 | Lee et al. |
| 7,867,241 B2 | 1/2011 | Brock et al. |
| 9,351,759 B2 * | 5/2016 | Bonadio ............ A61B 17/3423 |
| 2001/0013764 A1 | 8/2001 | Blumenkranz et al. |

(56) References Cited

U.S. PATENT DOCUMENTS

| | | | |
|---|---|---|---|
| 2002/0091374 A1 | 7/2002 | Cooper | |
| 2005/0021050 A1 | 1/2005 | Cooper | |
| 2007/0299387 A1 | 12/2007 | Williams et al. | |
| 2008/0045803 A1* | 2/2008 | Williams | A61B 1/00052 600/204 |
| 2008/0147091 A1 | 6/2008 | Cooper | |
| 2008/0188868 A1* | 8/2008 | Weitzner | A61B 1/0014 606/130 |
| 2008/0269562 A1* | 10/2008 | Marescaux | A61B 1/00087 600/142 |
| 2009/0024141 A1* | 1/2009 | Stahler | A61B 34/71 606/130 |
| 2010/0063354 A1* | 3/2010 | Hashimoto | A61B 17/29 600/106 |
| 2010/0204713 A1 | 8/2010 | Ruiz Morales | |
| 2010/0224022 A1 | 9/2010 | Choi et al. | |
| 2011/0028990 A1 | 2/2011 | Cooper | |
| 2011/0066161 A1 | 3/2011 | Cooper | |
| 2011/0118543 A1* | 5/2011 | Dosher | A61B 17/3421 600/104 |
| 2011/0118545 A1 | 5/2011 | Williams et al. | |
| 2011/0152609 A1* | 6/2011 | Trusty | A61B 1/00149 600/102 |
| 2011/0213384 A1 | 9/2011 | Jeong | |
| 2011/0230723 A1* | 9/2011 | Castro | A61B 17/3421 600/205 |
| 2014/0012287 A1 | 1/2014 | Oyola et al. | |
| 2015/0105629 A1 | 4/2015 | Williams et al. | |

FOREIGN PATENT DOCUMENTS

| | | |
|---|---|---|
| EP | 1015068 | 9/2011 |
| WO | 2012015659 | 2/2012 |

OTHER PUBLICATIONS

International Search Report dated Dec. 9, 2013 issued in International application No. PCT/US2013/054326.
Expo-70 Robot—Vadim Matskevich's students, http://cyberneticzoo.com/wp-content/uploads/2010/03/Expo-70-MK-1969-02-p31-3.pdf, 1969.
Conductor Robot, http://cyberneticzoo.com/wp-content/uploads/2010/03/Ticket-robot-russian-1973.pdf, 1973.
Michael L. Rhodes, "Computer Graphics and an Interactive Stereotactic System for CT-Aided Neurosurgery", IEEE Computer Graphics and Application, Computer Graphics in Medicine & Biology, 1983, p. 31-37.
Lee E. Weiss, Arthur C. Sanderson, Charles P. Neuman, "Dynamic Sensor Based Control of Robots with Visual Feedback", IEEE Journal of Robotics and Automation, 1987, p. 404-417.
Jean-Jacques E. Slotine, Weiping Li, "Composite adaptive control of robot manipulators", Automatica; Nonlinear Systems Laboratory, Massachusetts Institute of Technology, Cambridge, MA 02139, U.S.A., 1989, p. 509-519.
Weiping Li, Jean-Jacques E. Slotine, "An indirect adaptive robot controller", Systems & Control Letters; Nonlinear Systems Laboratory, Massachusetts Institute of Technology Cambridge, MA 02139, U.S.A., 1989, p. 259-266.
Xu Hongbin, "Stability and performance robustness analysis of hybrid control for robot manipulators", Journal of UEST of China, vol. 22 No. 5, Oct. 1993, p. 501-505.
Francois Chaumette, Patrick Rives, Bernard Espiau, "Positioning of A Robot With Respect to An Object, Tracking It and Estimating Its Velocity by Visual Servoing", IEEE International Conf. on Robotics and Automation, 1991, p. 2248-2253.
A.V. Timofejev, N.V. Ivanova, "Expert System of the Control Programs Designing of Adaptive Robots", The Lenigrand Institute of Aircraft Instrumentation, 1991, p. 912-915.
W Szczepiński, "Theory of polyhedrons of positioning accuracy of manipulators", Mechanism and Machine Theory; Institute of Fundamental Technological Research, Polish Academy of Sciences, 00-049 Warsaw, Swietokrzyska 21, Poland, 1991, p. 697-709.
Junji Furusho, Hiroshi Nagao, Naruse Makoto, "Multivariable Root Loci of Control Systems of Robot Manipulators with Flexible Driving Systems* : Distortion Feedback", JSME International Journal, 1992, p. 65-73.
Potemkin, E., Astafurov, P., Osipov, A., Malenkov, M., Mishkinyuk, V., Sologub, P., "Remote-controlled robots for repair and recovery in the zones of high radiation levels", Robotics and Automation, IEEE, 1992, p. 80-82.
S. L. Shishkin, "Adaptive control of a biped robot walking across a horizontal plane", International Journal of Adaptive Control and Signal Processing, 1992, p. 259-264.
Henk Nijmeijer, "Global regulation of robots using only position measurements", Systems and Control Letters; Department of Electrical Engineering, Mechatronics Research Centre Twente, University of Twente, P.O. Box 217, 7500 AE Enschede, Netherlands, 1992, p. 289-293.
Hitoshi Maekawa, Kazuhito Yokoi, Kazuo Tanie, Makoto Kaneko, Nobuo Kimura, Nobuaki Imamura, "Development of a three-fingered robot hand with stiffness control capability", Mechatronics; Mechanical Engineering Laboratory, 1992, p. 483-494.
J.D. Moon, D.W. Cho, "A component mode synthesis applied to mechanisms for an investigation of vibration", Journal of Sound and Vibration; Department of Mechanical Engineering, Pohang Institute of Science and Technology, Pohang, Korea, 1992, p. 67-79.
Timopheev, A.V., Prokhorov, D.V., "Neural networks processing systems in recognition and control problems", Neuroinformatics and Neurocomputers; IEEE, 1992, p. 820-828.
Jianguo Fu, Naresh K. Sinha, "An iterative learning scheme for motion control of robots using neural networks: A case study", Journal of Intelligent & Robotic Systems, 1993, p. 375-398.
Troccaz, J. Lavallee, S. Hellion, E., "A passive arm with dynamic constraints: a solution to safety problems in medical robotics", Systems Engineering in the Service of Humans', Conference Proceedings, 1993, p. 166-171.
Swarup, M. Gopal, "Comparative study on linearized robot models", Journal of Intelligent & Robotic Systems, 1993, p. 287-300.
H. Azaria, A. Dvir, "Algorithm optimization using a rule-based system. A case study: The Direct Kinematic Solution in robotics", Journal of Intelligent & Robotic Systems, 1993, p. 309-324.
Erick Garcia-Benitez; Stephen Yurkovich; Kevin M. Passino, "Rule-Based Supervisory Control of a Two-Link Flexible Manipulator", Journal of Intelligent and Robotic Systems, 1993, p. 195-213.
K. Periyasamy, V. S. Alagar, T. D. Bui, "A formal framework for design and verification of robotic agents", Journal of Intelligent & Robotic Systems, 1993, p. 173-200.
S. Nicosia, A. Tornambè, P. Valigi, "State estimation in robotic manipulators: Some experimental results", Journal of Intelligent & Robotic Systems,, 1993, p. 321-351.
Dimitrios M. Emiris, Vassilios D. Tourassis, "Singularity-robust decoupled control of dual-elbow manipulators", Journal of Intelligent & Robotic Systems, 1993, p. 225-243.
M.M. Bayoumi, "Adaptive Control of Robots with Rigid Links: A Status Report", Department of Electrical Engineering, Queen's University, Ontario, Canada (IEEE), 1993, p. 232-236.
Y. Edan, B. A. Engel, G. E. Miles, "Intelligent control system simulation of an agricultural robot", Journal of Intelligent & Robotic Systems, 1993, p. 267-284.
Chun-Yi Su, "Adaptive sliding mode control of nonlinear robotic systems with time-varying parameters", Systems and Control Letters; Department of Mechanical Engineering, University of Victoria, Victoria, B.C. Canada V8W 3P6, 1993, p. 35-41.
Yalou Huang; Guizhang Lu, "Force Analysis and Hybrid Control Scheme for Multiple Robot Manipulators", Artificial Intelligence and Robotics Research Laboratories; Dept of Computer and System Sciences; Nankai University, China (Proceedings of the 1993 IEEE/RSJ International Conference on Intelligent Robots and Systems in Japan), 1993, p. 1530-1534.
C.M. Lim; T. Hiyama, "Experimental implementation of a fuzzy logic control scheme for a servomotor", Mechatronics; Department of Electronic Engineering, Ngee Ann Polytechnic, Singapore 2159 Singapore.

(56) References Cited

OTHER PUBLICATIONS

E. Al-Gallaf, A.J. Allen, K. Warwick, "Dextrous hands: Issues relating to a four-finger articulated hand", Mechatronics; Department of Cybernetics, School of Engineering and Information Sciences, University of Reading, Reading, Berks RG6 2AY, U.K., 1993, p. 329-342.
A. Swarup, M. Gopal, "On robustness of decentralized control for robot manipulators", Robotics and Autonomous Systems; Department of Electrical Engineering, Indian Institute of Technology, New Delhi—110016, India, 1993, p. 109-112.
L. Behera, M. Gopal, Santanu Chaudhury, "Trajectory tracking of robot manipulator using Gaussian networks", Dept. of Electrical Engineering, Indian Institute of Technology, Delhi, Hauz Khas, New Delhi 110 016, India, 1993.
E. V. Panteley, A. A. Stotsky, "Adaptive trajectory/force control scheme for constrained robot manipulators", International Journal of Adaptive Control and Signal Processing, 1993, p. 489-496.
Filaretov, V.F., "A Synthesis of Adaptive Control Systems for Industrial Robots ", Electronic Mfg Technology Symposium, 1993, p. 168-171.
S. Zenkevich, A. Maximov, A. Nazarova, A. Korshunov, "Control of robot-based assembly cell ", Lecture Notes in Control and Information Sciences , 1993, p. 418-427.
D.E. Whitney, "The Mathematics of Coordinated Control of Prosthetic Arms and Manipulators", Asme Publication, 1972.
Shapiro, "Digital Technology Enables Robots to See", Computer Design, 1978.
Bejczy, A. K., Salisbury, Jr., J. K., "Kinesthetic Coupling Between Operator and Remote Manipulator", Advances in Computer Technology, 1980.
"An Improved CT-Aided Stereotactic Neurosurgery Technique", Fifth Annual Symposium on Computer Applications in Medical Care, 1981, p. 591-595.
Michael L. Thodes, Ph.D, "Stereotactic Meurosurgery Using 3D Image Data From Computed Tomography", Journal of Medical Systems, 1982, p. 106-118.
Salisburg, Jr., J. Kenneth, "Kinematic and Force Analysis of Articulated Hands", 1982.
"Minicomputer Control Robot's Six Electrohydraulic Servoactuators", Hydraulics & Pneumatics, 1982, p. 53-58.
F.M. Kulakov, "Modeling Robot Control in Assembly Operations", Modern Robot Engineering Moscow, MIR Publishers, 1982, p. 100-116.
Bejczy et al., "Controlling Remote Manipulators Through Kinesthetic Coupling", Computers in Mechanical Engineering, 1983, p. 48-60.
L.E. Weiss, "Dynamic Visual Servo Control of Robots: an adaptive image-based approach, Technical Report", Part 1 Carnegie Mellon, 1984.
Dennis E. Bullard, "CT-Guided Stereotactic Biopsies Using a Modified Grame and Gildenberg Techniques", Journal of Neurology, Neurosurgery and Psychiatry, 1984, p. 590-595.
M. Caporali et al., "Design and Construction of a Five Fingered Robotic Hand", Robotics Age, 1984, p. 14-20.
Salisbury, Jr., J. K., "Design and Control of an Articulated Hand", International Symposium on Dessign and Synthesis, 1984.
L. Dade Lunsford, M.D., "Stereotactic Exploration of the Brain in the Era of Computed Tomography", Surg. Neurol, 1984, p. 222-230.
Jacobsen, S.C., Iversen, E.K., Knutti, D. F., Johnson, R.T., Biggers, K. B., "Design of the Utah/MIT Dexterous Hand", Conf. on Robotics and Automation, 1986.
S. Hayati, M. Mirmirani, "Improving the Absolute positioning Accuracy of Robot Manipulators", Journal of Robotic Systems, 1986, p. 397-413.
Vertut, J., Coiffet, P., "Teleoperations and Robotics Evolution and Development", Robot Technology, 1986, p. 191-194.
L.E. Weiss; A.C. Sanderson, "Dynamic Sensor-based Control of Robots with Visual Feedback", IEEE Journal of Robotics and Automation, 1987, p. 5.
Townsend, W.T., Salisbury, Jr. J. K., "The Effect of Coulomb Friction and Stiction on Force Control", Conf. on Robotics and Automation, 1987.
P. Rives, F. Chaumette, B. Espiau, "Visual Servoing Based on a Task Function Approach", International Symposium on Experimental Robotics (Canada), 1989.
B.L. Davies, R.D. Hibberd, A. Timoney, J.E.A. Wickham, "A surgeon robot for prostatectomies", Proc. of 2nd Int. Conference on Robotics in Medicine (UK), 1989.
J.T. Feddema, C.S.G. Lee, O.R. Mitchell, "Automatic selection of image features for visual servoing of a robot manipulator", Conf. IEEE Robotics and Automation (USA), 1989, p. 14-19.
J.T. Feddema, O.R. Mitchell, "Vision-Guided Servoing with Feature-Based Trajectory Generation", IEEE Transaction on Robotics and Automation, 1989.
Pierre J. de Smet, Eugene I. Rivin, Yongle Lou, D. Kegg, "Robot Performance as Influenced by Mechanical System", CIRP Annals—Manufacturing Technology, 1990, p. 383-386.
Mills, J.K., "Hybrid actuation of robotic manipulators: an integral manifold control approach", Intelligent Control, IEEE, 1990, p. 817-823.
John T. Feddema, C. S. George Lee, "Adaptive Image Feature Prediction and Control for Visual Tracking with A Hand-eye Coordinated Camera", IEEE Transactions on Systems, man, and Cybernetics, 1990, p. 1172-1183.
Rafiqul I. Noorani, "Microcomputer-based robot arm control", Mathematical and Computer Modelling, 1990, p. 450-455.
Elysseev S., Kuznetzov, N., Lukyanov A., "Control of Robot Vibrations", 1990.
C. Samson, B. Espiau, "Robot Control: The Task Function Approach", Oxford Univ., 1990.
Adams, L, Krybus, W., Meyer-Ebrecht, D., Rueger, R., Gilsbach, J.M., Moesges, R., Schloendorff, G., "Computer Assisted Surgery", IEEE Computer Graphics and Application, 1990, p. 43-51.
B. Espiau, F. Chaumette, P. Rives, "A new approach to visual servoing in robotics", Research Report; IRISA/INRIA (France), 1990.
Korikov, Anatoliim, Syriamkin, Vladimiri, Titov, Vitaliis, "Correlation robot vision systems", 1990, p. 264.
Sadegh N, Hopowitz R, "Stability and robustness analysis of a class of adaptive controller for robotic manipulator", The International Journal of Robotics Research, 1990.
Rocheleau, D.N., Crane, C.D., III, "Development of a graphical interface for robotic operation in a hazardous environment", Systems, Man, and Cybernetics, 1991, p. 1077-1081.
J.C. Latombe, "Robot Motion Planning", The Kluwer International Series in Engineering and Computer Science, Kluwer Academic Publishers, 1991.
Kubota, T., Sato, M., Harashima, F., "Visual Control of Robotic Manipulator Based on Neural Networks", Industrial Electronics, IEEE, 1992, p. 490-496.
Nakamura, H., Shimada, T., "An inspection robot for feeder cables-snake like motion control", Industrial Electronics, Control, Instrumentation, and Automation, 1992, p. 849-852.
P. Kazanzides, J, Zuhars, B, Mittelsstadt, R.H. Taylor, "Force sensing and control for a surgical robot", IEEE conference on Robotics and Automation (Nice), 1992, p. 612-617.
Vsevolod I. Astafyev Farus, Yakutsk, Russia Yuri M. Gorsky, "Homeostatics", Cybernetics and applied systems, 1992, p. 7-22.
S. Lavallee, J. Troccaz, L. Gaborit, A.L. Benabid, D. Hoffman, "Image guided operating robot: A clinical application in stereotactic neurosurgery", IEEE Conference on Robotics and Automation (Nice), 1992.
H.A. Paul, B. Mittelstadt, W.L. Bargar, B. Musits, R.H, Taylor, P. Kazanzides, J. Zuhars, B. Williamson, W. Hanson, "A surgical robot for total hip replacement surgery", IEEE Conference on Robotics and Automation (Nice), 1992, p. 606-611.
R.H. Taylor, et. al, Augmentation of Human Precision in Computer-Integrated Surgery, Innov. Tech. Biol. Med., 1992.
Takashi Matsui, Mochizuki Yoshihiro, Effect of Positive Angular Velocity Feedback on Torque Control of Hydraulic Actuator, JSME international journal, 1992, p. 406-412.

(56) References Cited

OTHER PUBLICATIONS

Ph, Cinquin, et. al, IGOR: Image Guided Operating Robot. Methodology, Medical Applications, Results, Innov. Tech. Biol. Med., 1992, p. 1048-1049.
Heung-Joo Jeon, Bum-Hee Lee, Robot Motion Planning for Time-Varying Obstacle Avoidance Using the Distance Function, 1992, p. 1429-1438.
Bose, B., Kalra, A.K., Thukral, S., Sood, A., Guha, S.K., Anand, S., Tremor Compensation for Robotics Assisted Microsurgery, Engineering in Medicine and Biology Society, 1992, p. 1067-1068.
Kenneth L. Hillsley, Stephen Yurkovich, Vibration Control of a Two-Link Flexible Robot Arm, Dynamics and Control, 1993, p. 261-280.
Canudas de Wit, C., Ortega, R., Seleme, S.I., Robot Motion Control Using Induction Motor Drives, Robotics and Automation, 1993, p. 533-538.
Alberto Rovetta, Xia Wen, Telemanipulation Control of a Robotic Hand With Cooperating Fingers by Means of Telepresence With a Hybrid Virtual-Real Structure, RoManSy 9: Proceedings of the Ninth CISM-IFToMM Symposium on Theory and Practice of Robots and.
James K. Mills, Hybrid Actuator for Robot Manipulators: Design, Controland Performance, Robotics and Automation, IEEE Conference, 1993, p. 19-38.
Pietro Fanghella, Carlo Galletti, An Approach to Symbolic Kinematics of Multiloop Robot Mechanisms, RoManSy9, 1993, p. 33-40.
Yozo Fujino, Pennung Warnitchai, B.M. Pacheco, Active Stiffness Control of Cable Vibration, Journal of Applied Mechanics, 1993, p. 948-953.
Ng, W.S. Davies, B.L. Hibberd, R.D. Timoney, A.G., Robotic Surgery, Engineering in Medicine and Biology Magazine, 1993, p. 120-125.
J.L. Dallaway, R.M. Mahoney, R.D. Jackson, R.G. Gosine, An Interactive Robot Control Environment for Rehabilitation Applications, Robotica, 1993, p. 541-551.
Giulio E. Lancioni, Domenico Bellini, Doretta Oliva, "A robot to provide multi-handicapped blind persons with physical guidance and activity choices", Journal of Developmental and Physical Disabilities, 1993, p. 337-348.
Melzer A, Schurr MO, Kunert W, Buess G, Voges U, Meyer JU., Intelligent Surgical Instrument System ISIS. Concept and Preliminary Experimental Application of Components and Prototypes, Endosc Surg Allied Technol., 1993, p. 165-170.
John G. Hunter, Jonathan M. Sackier, Minimally Invasive Surgery, McGraw Hill, Inc., Health Professions Division, 1993.
Zhao Yu-shan Gu Liang-xian , Generalized Dynamic Model for Multibodies Manipulator, 1993.
F.M. Kulakov, Russian Research on Robotics, Intelligent Autonomous Systems, 1995, p. 53-62.
Shevtsova N.A., Faure A., Klepatch A.A., Podladchikova L.N., Rybak I.A. , Model of Foveal Visual Preprocessor, Intelligent Robots and Computer Vision XIV: Algorithms, Techniques, Active Vision, and Material Handling, 1995, p. 588-596.
Reynolds, O., "On Efficiency of Belts or Straps as Communicators of Work", The Engineer, 1874, p. 396.
Swift, H. W., "Power Transmission by Belts: An Investigation of Fundamentals", The Institution of Mechanical Engineers, 1928.
Smith, G. A. et al., "Surgery", 1950, p. 817-821.
"Baby Robot", http://cyberneticzoo.com/wp-content/uploads/2010/03/Ticket-robot-russian-1973.pdf, 1970.
Rajac, "Variable-Pitch Transfer Mechanism", IBM Technical Disclosure Bulletin, 1974.
ZH Luo , "Theoretical and Experimental Study on Control of Flexible Robot Arms Using Direct Strain Feedback", 1992.
Bu Yonghong, Wang Yi, "The Identification of Geometric Link Parameters of Robot Manipulators", ACTAAutomatica Sinica, 1992.
Zheng Nanning Wang Long Hu chao Liu Jianqin, "Improved BP Neural Net and Its Application to Handwritten Numeral Recognition", 1992.
Stefano Chiaverini, Bruno Siciliano, Olav Egeland, Robot Control in Singular Configurations—Analysis and Experimental Results, Experimental Robotics II, 1993, p. 25-34.
Antonio Bicchi, J. Kenneth Salisbury, David L. Brock, Experimental Evaluation of Friction Characteristics With an Articulated Robotic Hand, Experimental Robotics II, 1993, p. 153-167.
Claudio Melchiorri, Gabriele Vassura, Mechanical and Control Issues for Integration of an Arm-Hand Robotic System, Experimental Robotics II, 1993, p. 136-152.
Andrew K, Rist, Ellen Y. Lin, Bartholomew O. Nnaji, RALPH Application for Surface Mount Assembly, International Journal of Flexible Manufacturing Systems, 1993, p. 27-52.
R.H. Taylor, et. al, A Model-Based Optimal Planning and Execution System With Active Sensing and Passive Manipulation for Augmentation of Human-Precision in Computer-Integrated Surgery, Lecture Notes in Control and Information Sciences; Experimental Robo.
Nobuyuki Furuya, Masatomo Matubara, An Algorithm of Motor Control by Software Servo System (2nd Report): Application to 4-Axes SCARA Robot, Journal of the Japan Society of Precision Engineering , 1993, p. 423-428.
H.S. Moon, S.Y. Lee, S.J. Na, A Study on Selection of Gas Metalarc Welding Parameters of Fillet Joints Using Neural Network, Journal of the Korean Welding Society, 1993, p. 151-160.
Byong Suk Kim, Computer—Assisted System for Accident Analysis and MUL-Function Protection in Industrial Robot, Papersearch. net (Korean Studies Information Co.), 1993, p. 61-64.
J. I. Arocena, R. W. Daniel, P. Elosegui, End Point Control of Compliant Robots, Experimental Robotics II, 1993, p. 435-449.
Ho Kyung Kim, Nonlinear Static Analysis and Determination of Initial Equilibrium States of Suspension Bridges, 1993, p. 177-186.
Gimdongha, imhyeongyo (Dong Ha Kim, Hyeon Kyo Lim), Safe Speed Limit of Robot Arm During Teaching and Maintenance Work, 1993, p. 64-70.
Chang-Boo Kim, Seung-Hoon Lee, Inverse Dynamic Analysis of a Felxible Robot Arm With Multiple Joints by Using the Optimal Control Method, Journal of the Korean Society of Precision Engineering, 1993, p. 133-140.
Chang-Soo Han, The Optimum Design of a 6 D.O.F. Fully-Parallel Micromanipulator for Enhanced Robot Accuracy, Journal of the Korean Society of Precision Engineering , 1993, p. 42-51.
Nicholas Jackson, The Story Behind the Russian Robot Collie Patent Sketches, The Atlantic, 2011.
Oh Joong Chan, Jong Sik Boong, Choi Ko Bong, Kwon Key Jo, Design a Mobile Robot's Tracking Control System Using Fuzzy Theory, Sung Kyun Kwan Univ., 1992, p. 112-115.
Sang-Gwon Lim, Jin-Won Lee, Yong-Ky Moon, Dong-Lyeol Jeon, Sang-Hyun Jin, In-Hwan Oh, Dong-Il Kim, Sung-Kwun Kim, Development of AC Servo Motor Controller for Industrial Robot and CNC Machine System, Control R/D Team, Samsung Electronics, 1992, p. 1211-1214.
E.S. Jeon, S.H. Park, J.E. Oh, Singylarty Control of Robot Wrist Joints Using Euler Parameters, Journal of the Korean Society of Precision Engineering , 1992, p. 11-152.
Yoon Seok Chang, Hakil Kim, Motion Estimation of Moving Objects Using Frequency Domain Transforms, 1992, p. 92-99.
Nam Gu Lee, Chong Soo Lee, Chong Kug Park, Dynamic Hybrid Position/Force Controller for Two Cooperating Robots, 1992, p. 103-107.
Jong-Wu Moon, Jeung Park, Chong-Xuk Park, Adaptibe Control of a Flexible Robot Manipulator—Using ARMA Prediction Model, 1992, p. 122-127.
Dae-Gab Gweon, Choong-Min Jung, Development of a Robot Wrist for the Assembly of Chamferless Parts, Journal of the Korean Society of Precision Engineering , 1992, p. 36-43.
Fumio Harashima, Yaskuhiko Dote, Sensor-Based Robot Systems, Proc. IEEE Int. Symposium; Muroran Institute of Tech. (Japan), 1992, p. 10-19.

(56) References Cited

OTHER PUBLICATIONS

Chang-Boo Kim, Seung-Hoon Lee, Formulation of the Equation of Motion for Flexible Robotics Arms by Using the Finite Element Method, Inha Univ., Daewoo Heavy Industries Ltd, 1992, p. 233-238.

Jin-Geol Kim, A Study on the Robust Digital Tracking Control of a Robot With Flexible Joints, Journal of the Korean Society of Precision Engineering , 1992, p. 92-100.

Han-Sig Lee, The Prospects for the Future on Research of Flexible Automation and Robot System, 1992, p. 37-38.

Young Hood Joo, Seok Joo Yi, San Yeob Cha, Kwang Bang Woo, Hyung Woo Yoon, Gun Woong Hae, Sung Kwun Kim, A Study on Optimal Navigation of Autonomous Mobile Robot, Production of Eng. Division, Samsung Electronics Co., 1992, p. 128-133.

H. C. Shen, W. P. Yan, G. E. Taylor, Intelligent Sensory Decision-Making for Error Identification in Autonomous Robotics Systems, The International Journal of Advanced Manufacturing Technology, 1993, p. 377-384.

Morris R. Driels, W. Swayze, S. Potter, Full-Pose Calibration of a Root Manipulator Using a Coordinate-Measuring Machine, The International Journal of Advanced Manufacturing Technology, 1993, p. 34-41.

M. Wu, B. C. Jiang, Y. R. Shiau, Controlling a Robot's Position Using Neural Networks, The International Journal of Advanced Manufacturing Technology, 1993, p. 216-226.

Joachim O. Berg, Path and Orientation Accuracy of Industrial Robots, The International Journal of Advanced Manufacturing Technology, 1993, p. 29-33.

Shaheen Ahmad, Mohamed Zribi, Lyapunov-Based Control Design for Multiple Robots Handling a Common Object, Dynamics and Control, 1993, p. 127-157.

S.D. Park, K.W. Jeong, W.K. Chung, Y. Youm, Development of a Control Method Using Both Electric and Pneumatic Actuators For a Heavy Load Handing Robot, Journal of the Korean Society of Precision Engineering , 1993, p. 14-21.

Nicolay V. Kim, Algorithms of Observation Information Synthesis, International Conference on Electronics, Informations and Communications, 1993, p. 120-124.

Sung Do Chi, Seok Pil Lee, Wang Jae Lee, San Hui Park, Hierarchical Design of Intelligent Robot System, Hankuk Aviation Univ., Yonsel Univ., 1993, p. 213-216.

Cai Zi-Xing, Jiang Zhiming, High-Level Expert System-Based Robot Planning, 1993.

Yong-Deuk Seo, Dong-Joon Choi, Ki-Sang Hong, Hong Joeng, The Development of Intelligent Robot Using Vision and Speech Recognition System, Department of EE, POSTECH, 1993, p. 39-44.

Jae-Hun Jung, Yong-Hyun Jung, Jong-Mo Kim, Suck-Gyu Lee, Dal-Hae Lee, Motion Control of Autonomous Mobile Robot With Fuzzy Algorithm, Yeungnam Univ., 1993, p. 362-365.

Jin-Seob Choi, Dong-Won Kim, Sung-Mo Yang, A Study on the Pseudoinverse Kinematic Motion Control of 6-Axis Arc Welding Robot, Journal of the Korean Society of Precision Engineering , 1993, p. 170-177.

A Study on a Basic System Configuration for the PC Interface and the Robot Trajectory Generation, 1993, p. 354-358.

G,T. Yang, S.D. Ahn, S.C. Lee, Tip Position Control of Flexible Robot Arm by Self-Tuning Fuzzy Algorithm, Chonbuk Univ., 1993, p. 213-217.

Jeong Park, Hoe-Young Yoo, The Study of the Method of Position Control for the One-Link Flexible Robot Arm, 1993, p. 57-60.

ASEA Industrial Robot System IRb-60, 1975, p. 1-8.

Robots Take a Hold on Production, 1982, p. 122-129.

M. Peter Heilburn, M.D., J., Preliminary Experience With Brown-Robert-Wells (BRW) Computerized Tomography Stereotaxis Guidance System, Neurourgery, 1983, p. 217-221.

International Machine Intelligence Robot System Users Manual, International Machine Intelligence, 1983.

Orbitran Wafer Handling Robot, Genmark Automation, 1989, p. 2,3,4.

H Kojima, R Toyama, Development of Wall Cleaning Robot, 1992.

L.E. Weiss, "Dynamic Visual Servo Control of Robots: an adaptive image-based approach, Technical Report", Part 2 Carnegie Mellon, 1984.

L.E. Weiss, "Dynamic Visual Servo Control of Robots: an adaptive image-based approach, Technical Report", Part 3 Carnegie Mellon, 1984.

\* cited by examiner

SURGICAL TOOL POSITIONING SYSTEM

RELATED APPLICATIONS

This application claims the benefit of U.S. Provisional Application No. 61/681,340, filed Aug. 9, 2012, the content of which is incorporated herein by reference in its entirety.

This application claims the benefit of U.S. Provisional Application No. 61/751,498, filed Jan. 11, 2013, the content of which is incorporated herein by reference in its entirety.

This application claims the benefit of U.S. Provisional Application No. 61/825,297, filed May 20, 2013, the content of which is incorporated herein by reference in its entirety.

This application claims the benefit of U.S. Provisional Application No. 61/818,878, filed May 2, 2013, the content of which is incorporated herein by reference in its entirety.

This application is related to PCT Application No. PCT/US2012/040414, filed Jun. 1, 2012, the content of which is incorporated herein by reference in its entirety.

This application is related to U.S. Provisional Application No. 61/492,578, filed Jun. 2, 2011, the content of which is incorporated herein by reference in its entirety.

This application is related to PCT Application No PCT/US2012/032279, filed Apr. 5, 2012, the content of which is incorporated herein by reference in its entirety.

This application is related to U.S. Provisional Application No. 61/472,344, filed Apr. 6, 2011, the content of which is incorporated herein by reference in its entirety.

This application is related to PCT Application No PCT/US2011/060214, filed Nov. 10, 2011, the content of which is incorporated herein by reference in its entirety.

This application is related to U.S. Provisional Application No. 61/412,733, filed Nov. 11, 2010, the content of which is incorporated herein by reference in its entirety.

This application is related to PCT Application No PCT/US2012/054802, filed Sep. 12, 2012, the content of which is incorporated herein by reference in its entirety.

This application is related to U.S. Provisional Application No. 61/534,032, filed Sep. 13, 2011, the content of which is incorporated herein by reference in its entirety.

This application is related to U.S. Provisional Application No. 61/406,032, filed Oct. 22, 2010, the content of which is incorporated herein by reference in its entirety.

This application is related to PCT Application No PCT/US2011/057282, filed Oct. 21, 2011, the content of which is incorporated herein by reference in its entirety.

This application is related to U.S. Provisional Application No. 61/368,257, filed Jul. 28, 2010, the content of which is incorporated herein by reference in its entirety.

This application is related to PCT Application No PCT/US2011/044811, filed Jul. 21, 2011, the content of which is incorporated herein by reference in its entirety.

This application is related to PCT Application No PCT/US2012/070924, filed Dec. 20, 2012, the content of which is incorporated herein by reference in its entirety.

This application is related to U.S. Provisional Application No. 61/578,582, filed Dec. 21, 2011, the content of which is incorporated herein by reference in its entirety.

This application is related to PCT Application No PCT/US2013/043858, filed Jun. 3, 2013, the content of which is incorporated herein by reference in its entirety.

This application is related to U.S. patent application Ser. No. 11/630,279, filed Dec. 20, 2006, published as U.S. Patent Application Publication No. 2009/0171151, the content of which is incorporated herein by reference in its entirety.

TECHNICAL FIELD

The present inventive concepts generally relate to the field of robotics, and more particularly, to multi-operator robotic systems for medical applications.

BACKGROUND

As less invasive medical techniques and procedures become more widespread, medical professionals, such as surgeons or other clinicians, may require articulating surgical tools to perform such less invasive medical techniques and procedures from outside the human body. Conventional articulating surgical tools such as endoscopes and the like can be operated by a surgeon or other clinician at a single operator location.

SUMMARY

In one aspect, a tool positioning system comprises an introduction device constructed and arranged to slidingly receive an articulating probe; a first tool support comprising at least one guide element constructed and arranged to slidingly receive a first tool, wherein the first tool support is oriented toward a first operator location; and a second tool support comprising at least one guide element constructed and arranged to slidingly receive a second tool, wherein the second tool support is oriented toward a second operator location.

In some embodiments, at least one of the first tool or the second tool is positioned at a patient to perform a medical procedure on the patient.

In some embodiments, the medical procedure comprises a transoral surgery procedure.

In some embodiments, the transoral surgery procedure includes a resection at or near at least one of a base of a tongue, tonsils, a base of a skull, a hypopharynx, a larynx, a trachea, an esophagus, a stomach, or a small intestine.

In some embodiments, the medical procedure includes at least one of a single or multiport transaxilla, thoracoscopic, pericardial, laparoscopic, transgastric, transenteric, transanal, or transvaginal procedure.

In some embodiments, the single or multiport transaxilla procedure includes a laryngectomy.

In some embodiments, the single or multiport thoracoscopic procedure includes a mediastinal nodal dissection.

In some embodiments, the single or multiport pericardial procedure includes measuring and treating arrhythmias.

In some embodiments, the single or multiport single or multiport laparoscopic procedure includes a revision of bariatric lap-band procedures.

In some embodiments, the single or multiport transgastric or transenteric procedure includes at least one of a cholecystectomy or a splenectomy.

In some embodiments, the single or multiport transanal or transvaginal procedure includes at least one of a hysterectomy, oophorectomy, cystectomy or colectomy.

In some embodiments, the first tool support is coupled to the second tool support.

In some embodiments, the first tool support and the second tool support are coupled to each other at a common element.

In some embodiments, a connection at the common element maintains a fixed distance between the first tool support and the second tool support.

In some embodiments, a connection at the common element maintains a fixed orientation between the first tool support and the second tool support.

In some embodiments, the at least one of the first and second tool supports moves linearly relative to the common element.

In some embodiments, the first tool support and second tool support are fixed in position relative to each other.

In some embodiments, positions of the first and second tool supports are maintained during an operation of the tool positioning system.

In some embodiments, the first tool support and second tool support are fixed in orientation relative to each other.

In some embodiments, orientations of the first and second tool supports are maintained during an operation of the tool positioning system.

In some embodiments, at least one of the first tool support or second tool support is rotatable relative to the other.

In some embodiments, at least one of the first tool support or the second tool support is rotatable relative to the other at a common element to which each of the first and second tool supports is coupled.

In some embodiments, at least one of the first and second tool supports is locked in a fixed position relative to the common element.

In some embodiments, the system further comprises a locking mechanism that locks the at least one of the first and second tool supports in the fixed position.

In some embodiments, at least one of the first tool support and the second tool support is directly anchored to the introduction device.

In some embodiments, at least one of the first tool support and second tool support is bonded to the introduction device.

In some embodiments, at least one of the first tool support and second tool support is welded to the introduction device.

In some embodiments, the system further comprises a base, wherein the first tool support and the second tool support are coupled to the base.

In some embodiments, the introduction device is coupled to the base.

In some embodiments, the base comprises a collar that surrounds at least a portion of the introduction device.

In some embodiments, the collar extends in a lateral direction relative to a direction of extension of the introduction device.

In some embodiments, the collar has first and second openings aligned with the first and second tool supports.

In some embodiments, the collar has first and second openings, wherein the first and second tool supports extend through the first and second openings.

In some embodiments, at least one of the first tool support or the second tool support comprises at least one guide element that rotatably engages the base.

In some embodiments, the at least one of the first tool support and the second tool support comprises a gimbal which rotatably engages the at least one guide element at the base.

In some embodiments, the least one guide element of the first tool support comprises a mid-portion that rotatably engages the base.

In some embodiments, the first tool support rotatably engages the base and the second tool support rotatably engages the base.

In some embodiments, the at least one guide element of the first tool support is fixedly attached to the base.

In some embodiments, the at least one guide element of the first tool support comprises a mid-portion that rotatably engages the base.

In some embodiments, the at least one of the first or second tool supports moves linearly relative to the base.

In some embodiments, the system is constructed and arranged to slidingly receive two tools.

In some embodiments, the system is constructed and arranged to slidingly receive three tools.

In some embodiments, the system is constructed and arranged to slidingly receive four tools.

In some embodiments, the system is constructed and arranged to slidingly receive five or more tools.

In some embodiments, the at least one guide element of the first tool support is constructed and arranged to receive a shaft of the first tool, and wherein the at least one guide element of the second tool support is constructed and arranged to receive a shaft of the second tool.

In some embodiments, the first tool is positioned at a first side of a distal end of the articulating probe and the second tool is positioned at a second side of the distal end of the articulating probe relatively opposite the first side.

In some embodiments, the first tool is controlled by an operator at the first operator location at the first side of the distal end of the articulating probe, and the second tool is controlled by an operator at the second operator location at the second side of the distal end of the articulating probe.

In some embodiments, the first tool and a third tool are positioned at a first side of a distal end of the articulating probe and the second tool and a fourth tool are positioned at a second side of the distal end of the articulating probe relatively opposite the first side.

In some embodiments, the first and third tools are controlled by an operator at the first operator location at the first side of the distal end of the articulating probe, and the second and fourth tools are controlled by an operator at the second operator location at the second side of the distal end of the articulating probe.

In some embodiments, at least one of the first tool support or the second tool support comprises a funnel shaped proximal end.

In some embodiments, at least one guide element of at least one of the first tool support or the second tool support comprises an inner guide element and an outer guide element.

In some embodiments, the outer guide element comprises a first tube and the inner guide element comprises a second tube slidingly positioned in the first tube.

In some embodiments, the inner guide element movably extends from the outer guide element.

In some embodiments, at least a portion of the inner guide element is flexible.

In some embodiments, the system further comprises a third tool support, the third tool support comprising at least one guide element constructed and arranged to slidingly receive a third tool.

In some embodiments, the third tool support is oriented toward the first operator location.

In some embodiments, the system further comprises a connector coupled to the first tool support and the third tool support, wherein the connector is constructed and arranged to maintain a relative position between the first tool support and the third tool support.

In some embodiments, the system further comprises a fourth tool support, the fourth tool support comprising at least one guide element constructed and arranged to slidingly receive a fourth tool.

In some embodiments, the fourth tool support is oriented toward the second operator location.

In some embodiments, the system further comprises a connector coupled to the second tool support and the fourth tool support, wherein the connector is constructed and arranged to maintain a relative position between the second tool support and the fourth tool support.

In some embodiments, the system further comprises a connector coupled to a proximal end of each of the first and third tool supports, and a connector attached to a proximal end of each of the second and fourth tool supports.

In some embodiments, the system further comprises a connector coupled to the first tool support and the second tool support, wherein the connector is constructed and arranged to maintain a relative position between the first tool support and second tool support.

In some embodiments, the connector is rotatably coupled to the first tool support.

In some embodiments, the connector is rotatably coupled to the first tool support and the second tool support.

In some embodiments, the connector is attached to a proximal end of the first and second tool supports.

In some embodiments, the connector extends in a direction that is transverse the directions of extension of proximal ends of the first and second tool supports.

In some embodiments, the system further comprises a fixation point on the connector constructed and arranged to attach to a stabilizing brace.

In some embodiments, the system further comprises a third tool support and a connector coupled to the first, second and third tool supports, wherein the connector is constructed and arranged to maintain a relative position between the first, second, and third tool supports.

In some embodiments, the at least one guide element of the first tool support or the second tool support comprises a hollow elongate member.

In some embodiments, the hollow elongate member comprises a structure selected from the group consisting of: a hollow tube, a coil such as a helical coil, a plastic tube such as a braided plastic tube, and combinations thereof.

In some embodiments, at least a portion of the hollow elongate member is rigid.

In some embodiments, at least a portion of the hollow elongate member is flexible.

In some embodiments the first operator location and the second operator location comprise side-by-side locations.

In some embodiments, the first tool support is constructed and arranged to provide tool access to a patient's head.

In some embodiments, the first tool support is constructed and arranged to provide tool access to a patient's esophagus.

In some embodiments, the first operator location and the second operator location comprise face-to-face locations.

In some embodiments, the first tool support is constructed and arranged to provide tool access to at least one of a patient chest or a patient abdomen.

In some embodiments, the system further comprises a fixation point constructed and arranged to attach to a stabilizing brace.

In some embodiments, the first tool support comprises the fixation point.

In some embodiments, the system further comprises a connector coupled to the first tool support and the second tool support.

In some embodiments, the connector is constructed and arranged to maintain a relative position between the first tool support and second tool support, wherein the connector comprises the fixation point.

In some embodiments, the introduction device comprises the fixation point.

In some embodiments, the system further comprises a base coupling the first tool support and the second tool support, wherein the base comprises the fixation point.

In some embodiments, the system further comprises a brace attachable to the fixation point.

In some embodiments, the brace is further attachable to a location selected from the group consisting of: a floor, a patient operating table, an articulating probe feeder, and combinations thereof.

In some embodiments, the system further comprises a second fixation point constructed and arranged to attach to a stabilizing brace.

In some embodiments, the system further comprises a first brace for attachment to the first fixation point and a second brace for attachment to the second fixation point.

In some embodiments, the system further comprises the articulating probe.

In some embodiments, the articulating probe comprises a distal link.

In some embodiments, the distal link comprises at least a first sideport coupled to the first tool support and a second sideport coupled to the second tool support.

In some embodiments, the system further comprises a third tool support, wherein the distal link comprises at least a first sideport coupled to the first tool support, a second sideport coupled to the second tool support and a third sideport coupled to the third tool support.

In some embodiments, the first, second and third sideports are symmetrically spaced about a periphery of the distal link.

In some embodiments, the first, second and third sideports are asymmetrically spaced about a periphery of the distal link.

In some embodiments, the first and second sideports are positioned 30° to 180° apart about a periphery of the distal link.

In some embodiments, the system further comprises a fourth tool support wherein the distal link further comprises a fourth sideport coupled to the fourth tool support.

In some embodiments, the system further comprises a fifth tool support wherein the distal link further comprise a fifth sideport coupled to the fifth tool support.

In some embodiments, the system further comprises a controller constructed and arranged to manipulate the articulating probe.

In some embodiments, the system further comprises a first human interface device oriented toward the first operator location, the first human interface generating a first control signal received by the controller for manipulating the articulating probe.

In some embodiments, the system further comprises a tool wherein the tool comprises the first human interface device.

In some embodiments, the system further comprises a second human interface device oriented toward the second operator location and constructed and arranged to generate a second control signal received by the controller for manipulating the articulating probe.

In some embodiments, the system further comprises a tool wherein the tool comprises the second human interface device.

In some embodiments, the system further comprises a connector coupled to the first tool support and the second tool support, wherein the connector is constructed and arranged to maintain a relative position between the first tool support and second tool support, wherein the first human interface device is positioned on the connector.

In some embodiments, the human interface device on the connector communicates with the controller via a wireless connection.

In some embodiments, the system further comprises at least one tool constructed and arranged to be slidingly received by at least one of the first tool support or the second tool support.

In some embodiments, the at least one tool comprises at least two tools, wherein each tool comprises a shaft constructed and arranged to be slidingly received by at least one of the first tool support or the second tool support.

In some embodiments, the at least one tool comprises a tool selected from the group consisting of: a suction device, a ventilator, a light, a camera, a grasper, a laser, a cautery, a clip applier, a scissors, a needle, a needle driver, a scalpel, an RF energy delivery device, a cryogenic energy delivery device, and combinations thereof.

In another aspect, a tool positioning system comprises a first tool support comprising at least one guide element constructed and arranged to slidingly receive a first tool, wherein the first tool support is oriented toward a first operator location; a second tool support comprising at least one guide element constructed and arranged to slidingly receive a second tool, wherein the second tool support is oriented toward a second operator location; and a base that couples the first tool support and the second tool support.

In some embodiments, the system further comprises an introduction device coupled to the base.

In some embodiments, the base comprises a collar that surrounds at least a portion of the introduction device.

In some embodiments, the collar extends in a lateral direction relative to a direction of extension of the introduction device.

In some embodiments, the collar has first and second openings aligned with the first and second tool supports.

In some embodiments, the collar has first and second openings, wherein the first and second tool supports extend through the first and second openings.

In some embodiments, at least one of the first tool support or the second tool support comprises at least one guide element that rotatably engages the base.

In some embodiments, the at least one of the first tool support and the second tool support comprises a gimbal which rotatably engages the at least one guide element at the base.

In some embodiments, the least one guide element of the first tool support comprises a mid-portion that rotatably engages the base.

In some embodiments, the first tool support rotatably engages the base and the second tool support rotatably engages the base.

In some embodiments, the at least one guide element of the first tool support is fixedly attached to the base.

In some embodiments, the at least one guide element of the first tool support comprises a mid-portion that rotatably engages the base.

In another aspect, a tool positioning system comprises a first tool support comprising at least one first guide element constructed and arranged to slidingly receive a first tool; a second tool support comprising at least one second guide element constructed and arranged to slidingly receive a second tool; and a first connector attached to the first tool support and the second tool support, wherein the connector is constructed and arranged to maintain a distance between the first tool support and second tool support.

In some embodiments, the first connector is fixedly attached to at least the first tool support or the second tool support.

In some embodiments, the first connector is rotatably attached to at least the first tool support or the second tool support.

In some embodiments, the system further comprises a gimbal which rotatably engages the at least one first or second guide element at the base.

In some embodiments, the first connector comprises a first opening and a second opening each constructed and arranged to operably engage a tool support of the first and second tool supports.

In some embodiments, the first opening and the second opening are constructed and arranged to position the first tool support and the second tool support in a non-parallel configuration.

In some embodiments, at least one of the first opening or the second opening comprises a funnel-shaped opening.

In some embodiments, the first connector further comprises a third opening constructed and arranged to operably engage a third tool support.

In some embodiments, a single operator operates a tool extending from each of the first, second, and third tool supports from an operator location.

In some embodiments, the first connector comprises a rigid structure.

In some embodiments, the first connector comprises at least a portion that is flexible.

In some embodiments, the first connector comprises an operator shapeable structure.

In some embodiments, the first connector comprises a malleable structure.

In some embodiments, the first connector comprises a hinged portion.

In some embodiments, the first connector is constructed and arranged to be shaped after at least one of the application of hear or the removal of heat.

In some embodiments, the first connector is constructed and arranged to be attachable to at least one of the first tool support or the second tool support.

In some embodiments, the first connector is constructed and arranged to be detachable to at least one of the first tool support or the second tool support.

In some embodiments, the system further comprises a second connector attachable to the first tool support and the second tool support, wherein the second connector is constructed and arranged to maintain a relative position between the first tool support and the second tool support.

In some embodiments, the first connector is constructed and arranged to position the first tool support and the second tool support in a first geometry, and the second connector is constructed and arranged to position the first tool support and the second tool support in a second geometry different than the first geometry.

In some embodiments, the first connector differs from the second connector by at least one of length, shape or curvature.

In some embodiments, the system further comprises a third tool support comprising at least one guide element constructed and arranged to slidingly receive a shaft of a tool.

In some embodiments, the first connector further maintains a relative position of the third tool support relative to the first tool support and the second tool support.

In some embodiments, the system further comprises a fourth tool support comprising at least one guide element constructed and arranged to slidingly receive a shaft of a tool.

In some embodiments, the system further comprises a second connector constructed and arranged to maintain a relative position between the second tool support and the fourth tool support, wherein the first connector is constructed and arranged to maintain a relative position between the first tool support and the third tool support.

In some embodiments, a single operator operates a tool extending from each of the first, second, and third tool supports from an operator location, In some embodiments, a first operator operates tools extending from two of the first, second, and third tool supports, and a second operator operates a tool extending from the other of the first, second, and third tool supports.

In some embodiments, the first connector can be removably coupled to the first and second tool supports.

In some embodiments, the first connector is replaced with a third connector having different dimensions than the first connector.

In some embodiments, the inventive concepts comprise an articulating probe as described in reference to the figures.

In some embodiments, the inventive concepts comprise a surgical tool as described in reference to the figures.

In some embodiments, the inventive concepts comprise a controller as described in reference to the figures.

In some embodiments, the inventive concepts comprise a method of controlling a robotic system as described in reference to the figures.

In some embodiments, the inventive concepts comprise a human interface device as described in reference to the figures.

In some embodiments, the inventive concepts comprise a method of performing a medical procedure as described in reference to the figures.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same elements throughout the different views. The drawings are not necessarily to scale, emphasis instead being placed upon illustrating the principles of the preferred embodiments.

DETAILED DESCRIPTION OF EMBODIMENTS

The terminology used herein is for the purpose of describing particular embodiments and is not intended to be limiting of the inventive concepts. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on" or "connected" or "coupled" to another element, it can be directly on or above, or connected or coupled to, the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.). When an element is referred to herein as being "over" another element, it can be over or under the other element, and either directly coupled to the other element, or intervening elements may be present, or the elements may be spaced apart by a void or gap.

Figure 1:
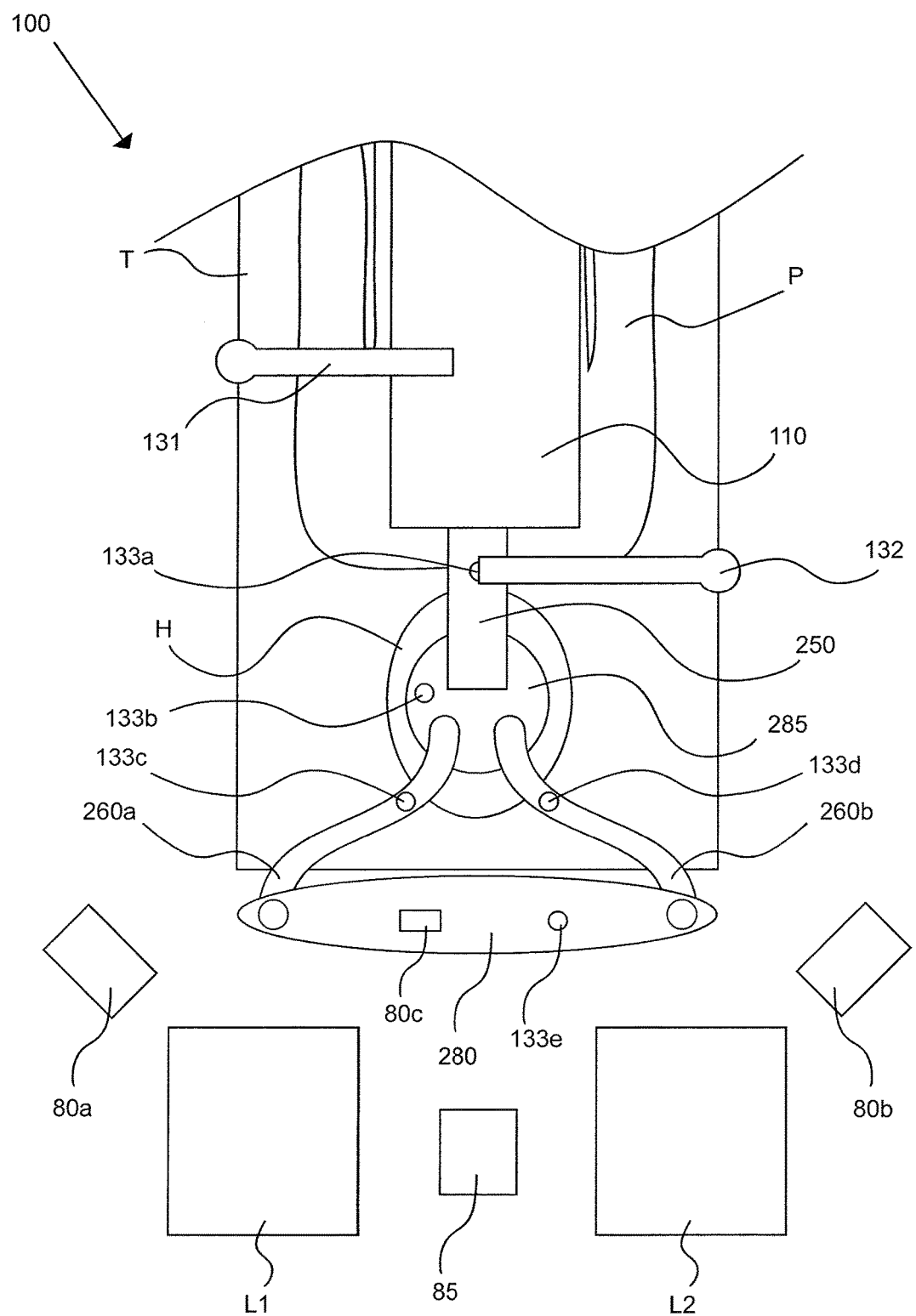
FIG. 1 is a top view of a tool positioning system for performing a medical procedure, in accordance with embodiments of the present inventive concepts.

FIG. 1 is a top view of a tool positioning system 100 for performing a medical procedure, in accordance with embodiments of the present inventive concepts. The tool positioning system 100 is constructed and arranged to position one or more tools (not shown in FIG. 1) for performing a medical procedure on a patient P, for example, a transoral robotic surgery procedure or the like. The medical procedure can include a surgical procedure that includes inserting one or more tools into a cavity of the patient (P), or a region of the patient (P) formed by an incision or related opening. A surgical procedure can include one or more transoral procedures. Typical transoral procedures include resections or other procedures performed at or near a location selected from the group consisting of: base of a tongue; tonsils; base of skull; hypopharynx; larynx; trachea; esophagus; stomach; small intestine; and combinations of these. Other procedures can include but not be limited to single or multiport transaxilla procedures, such as a laryngectomy, single or multiport thoracoscopic procedures, such as a mediastinal nodal dissection, single or multiport pericardial procedures, for example, related to measuring and treating arrhythmias, single or multiport laparoscopic procedures, such as revision of bariatric lap-band procedures, single or multiport transgastric or transenteric procedures, such as a cholecystectomy or splenectomy, and/or single or multiport transanal or transvaginal procedures, such as a hysterectomy, oophorectomy, cystectomy and colectomy.

Figure 5:
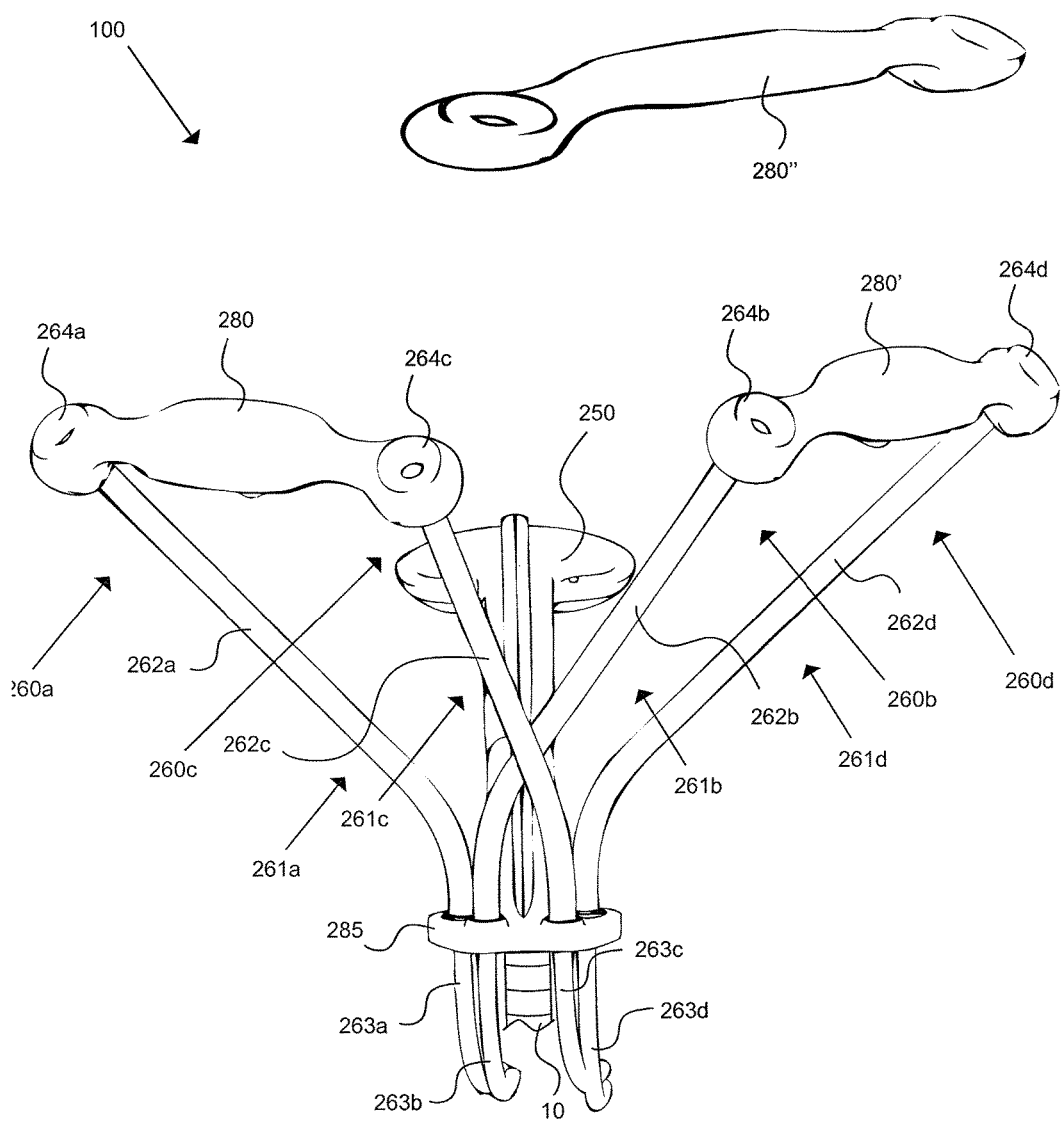
FIG. 5 is a perspective view of a tool positioning system having multiple connectors, in accordance with an embodiment of the present inventive concepts.

The tool positioning system 100 comprises an introduction device 250, a first tool support 260a, and a second tool support 260b. Although two tool supports 260a, 260b (generally, 260) are shown, the tool positioning system 100 can be constructed and arranged to include more than two tool supports 260. In one embodiment, as shown in FIG. 5, the tool positioning system 100 includes two, three, or four tool supports 260, each constructed and arranged to slidingly receive a tool, for example, a shaft of a tool. In other embodiments, the tool positioning system 100 includes five or more tool supports 260, each constructed and arranged to slidingly receive a tool.

Figure 4:
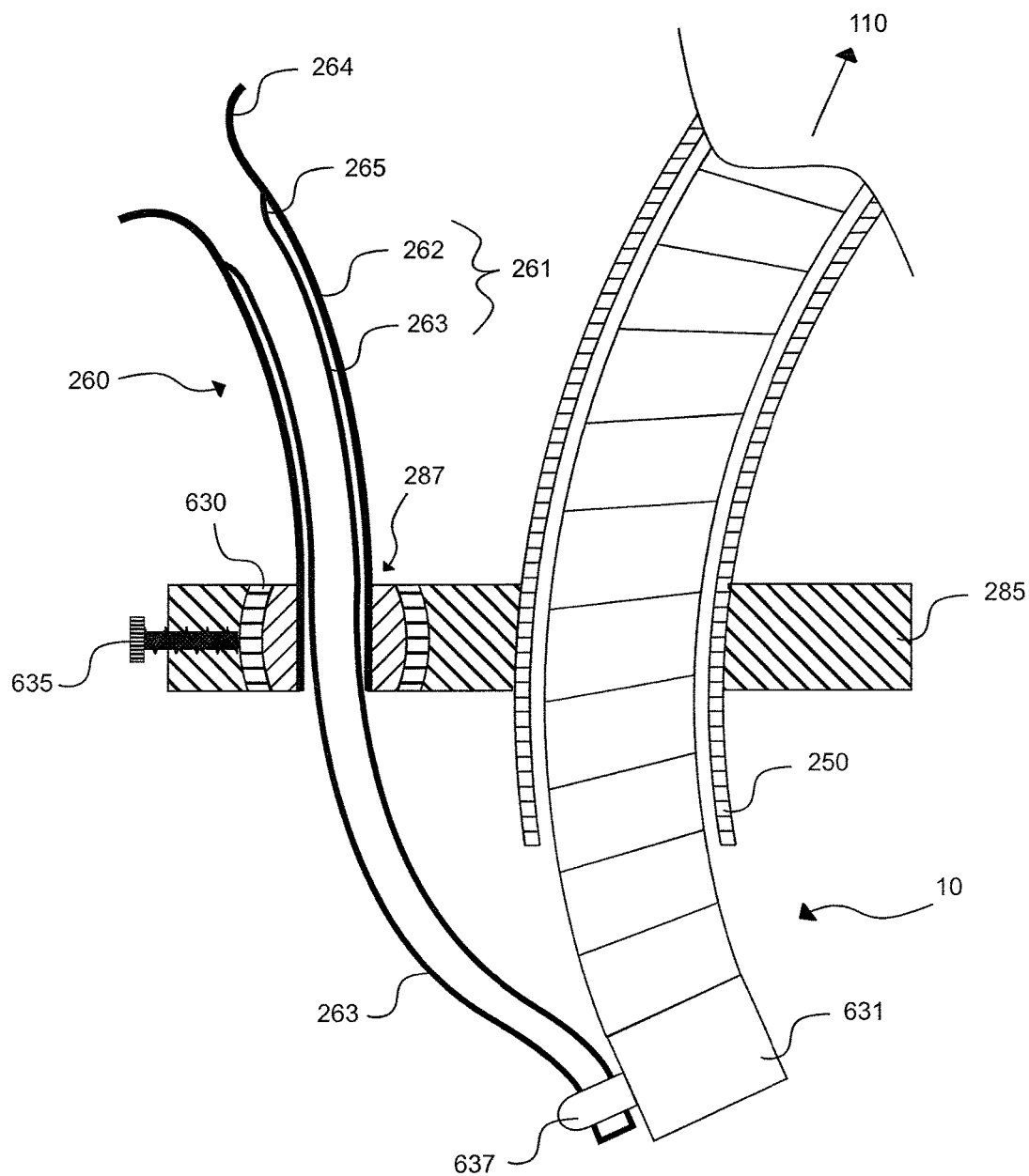
FIG. 4 is a cross-sectional front view of a tool positioning system, in accordance with embodiments of the present inventive concepts.

As shown in FIG. 4, the introduction device 250 can be constructed and arranged to slidingly receive an articulating probe such as the articulating probe 10, and support, stabilize, and/or guide the articulating probe to a region of interest. The region of interest may be a lumen of a body of a patient (P), such as a cavity at the patient's head (H), e.g., a nose or mouth, or an opening formed by an incision. In clinical applications, typical regions of interest can include but not be limited to the esophagus or other locations within the gastrointestinal tract, the pericardial space, the peritoneal space, and combinations thereof. The region of interest may alternatively be a mechanical device, a building, or another open or closed environment in which the probe 10 can be used.

The articulating probe 10 may be configured to guide one or more surgical tools, for example, during a medical procedure. The articulating probe 10 may include inner and outer sleeves, which can advance or retract with respect to one another during manipulation of the articulating probe 10. For example, the inner and outer sleeves of the articulating probe 10, which may include a plurality of inner links and a plurality of outer links (see FIG. 4), can be configured in one of a limp mode and a rigid mode so as to facilitate the manipulation of the articulating probe 10. For example, the inner and outer sleeves may be configured in one of the limp mode and the rigid mode via one or more steering cables (not shown) of the articulation probe 10.

The articulating probe 10 can be a highly articulated probe, for example, a highly articulated probe as described in U.S. Patent Application Publication No. 2009-0171151 entitled STEERABLE, FOLLOW THE LEADER DEVICE, U.S. Patent Publication No. 2008-0039690 entitled STEERABLE MULTI LINKED DEVICE HAVING MULTIPLE WORKING PORTS, or PCT Application No. PCT/US2011/044811 entitled "SURGICAL POSITIONING AND SUPPORT SYSTEM, each incorporated by reference in their entirety herein. The articulating probe 10 may include one or more light sources, image capturing devices, e.g., a camera, provided at the distal end of the articulating probe 10 and/or proximal the distal end of the tool supports 260.

Figure 7:
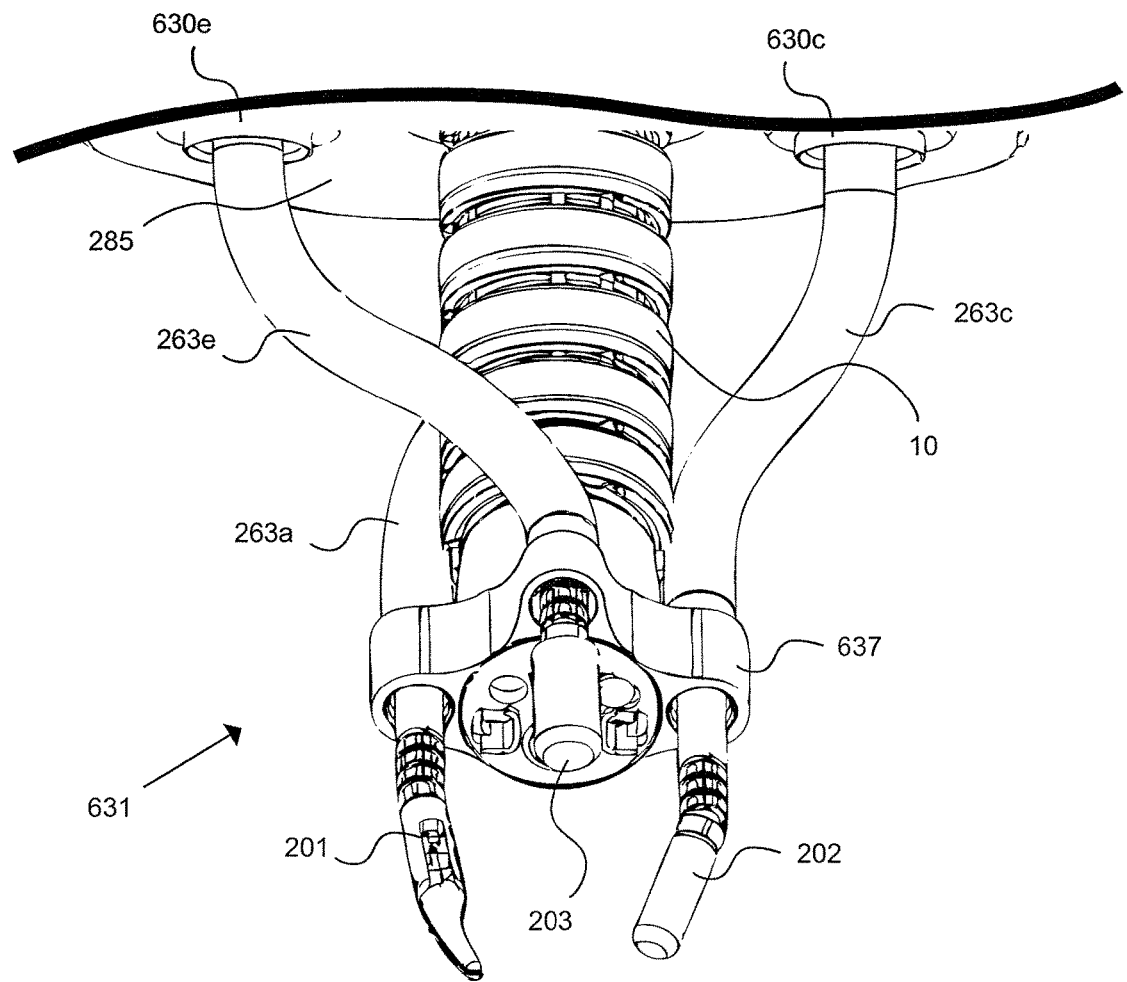
FIG. 7 is a perspective view of a distal end of a tool positioning system, in accordance with an embodiment of the present inventive concepts.

The articulating probe 10 comprises a feeder 110 which controllably advances one or more cables within an outer sleeve of the probe 10, such as a cable (not shown) extending to a distal link, for example, a distal link 631 shown in FIG. 7. The feeder 110 can comprise one or more cable control assemblies such as bobbin-driven motors and one or more link translating assemblies such as linearly advanceable carts.

Returning to FIG. 1, the first tool support 260a can be constructed and arranged to slidingly receive a shaft of a tool (not shown). The first tool support 260a is oriented toward a first operator location (L1). The second tool support 260b can also be constructed and arranged to slidingly receive a shaft of a tool (not shown). The second tool support 260b is oriented toward a second operator location (L2). The first and second tool supports 260a, 260b can have similar configurations, or different configurations such as different lengths. First and second tool supports 260a, 260b can be attached to one or more locations on the distal end of probe 10. In some embodiments, tool supports 260a, 260b are on opposite sides of the distal end of probe 10. In some embodiments, tool support 260a is attached to the same side of the distal end of probe 10 as operator location L1 is positioned (e.g. the left side of the page as shown), and tool support 260b is attached to the same side of the distal end of probe 10 as operator location L2 is positioned, e.g. the right side of the page as shown. Alternatively, tool support 260a is attached to the opposite side of the distal end of probe 10 as operator location L1 is positioned (e.g. the right side of the page), and tool support 260b is attached to the opposite side of the distal end of probe 10 as operator location L2 is positioned, e.g. the left side of the page. One operator can control a first tool at one side of the introduction device 250 at which extends from a distal end of the articulating probe 10. Another operator can control a second tool positioned at another side of the distal end of the articulating probe 10. In another embodiment, both operators can have tools positioned at both sides of the introduction device 250 and the distal end of the articulating probe 10.

The tool positioning system 100 can include a base 285. The base 285 can comprise openings for receiving the tool supports 260 and the introducer 250, which can be attached to the base 285 at their midportions, or at distal ends thereof. The first tool support 260a and the second tool support 260b are coupled to the base 285 to maintain a relative position between the first tool support 260a and the second tool support 260b and/or maintain a fixed orientation between the first tool support 260a and the second tool support 260b.

The base 285 can comprise a collar or the like that surrounds at least a portion of the introduction device 250. The collar can extend in a lateral direction relative to a direction of extension of the introduction device 250. As shown in FIG. 4, the base 285 can have an opening 287 aligned with a guide element 261 of each tool support 260. The guide element 261 can be affixed to the opening 287 of the base 285.

The tool positioning system 100 can include a connector 280, also referred to as a dogbone connector, coupled to the first tool support 260a and the second tool support 260b. The connector 280 is constructed and arranged to maintain a relative position between the first tool support 260a and the second tool support 260b. In some embodiments, connector 280 is constructed and arranged to maintain a relative orientation between the first tool support 260a and the second tool support 260b.

The connector 280 can comprise a rigid structure. The connector 280 can comprise at least a portion that is flexible. The connector 280 can comprise an operator shapeable structure. The connector 280 can comprise a malleable structure. The connector 280 can comprise two segments connected by a hinge, such as a butt hinge, a butterfly hinge, a barrel hinge or a hinge comprising a flexible portion positioned between two rigid portions. The connector 280 can comprise a telescopically adjustable structure, such as to allow separation of tool supports 260*a* and 260*b*. The connector 280 can comprise two segments connected by a rotatable connector, such as a universal joint.

The connector 280 can be constructed and arranged to be shaped, molded, or the like, such as after the application of heat. The connector 280 can be constructed and arranged to be attachable to at least one of the first tool support 260*a* or the second tool support 260*b*. The connector 280 can be constructed and arranged to be detachable to at least one of the first tool support 260*a* or the second tool support 260*b*.

An alternative connector can be provided, for example, connector 280" shown in FIG. 5, that is attachable to the first tool support 260*a* and the second tool support 260*b*. The alternative connector 280" can be constructed and arranged to maintain a relative position between the first tool support 260*a* and the second tool support 260*b*. The original connector 280 can be constructed and arranged to position the first tool support 260*a* and the second tool support 260*b* in a first geometry, and the alternative connector 280" can be constructed and arranged to position the first tool support 260*a* and the second tool support 260*b* in a second geometry different than the first geometry. The original connector 280 can differ from the alternative connector 280" by at least one of length, shape or curvature.

Figure 3:
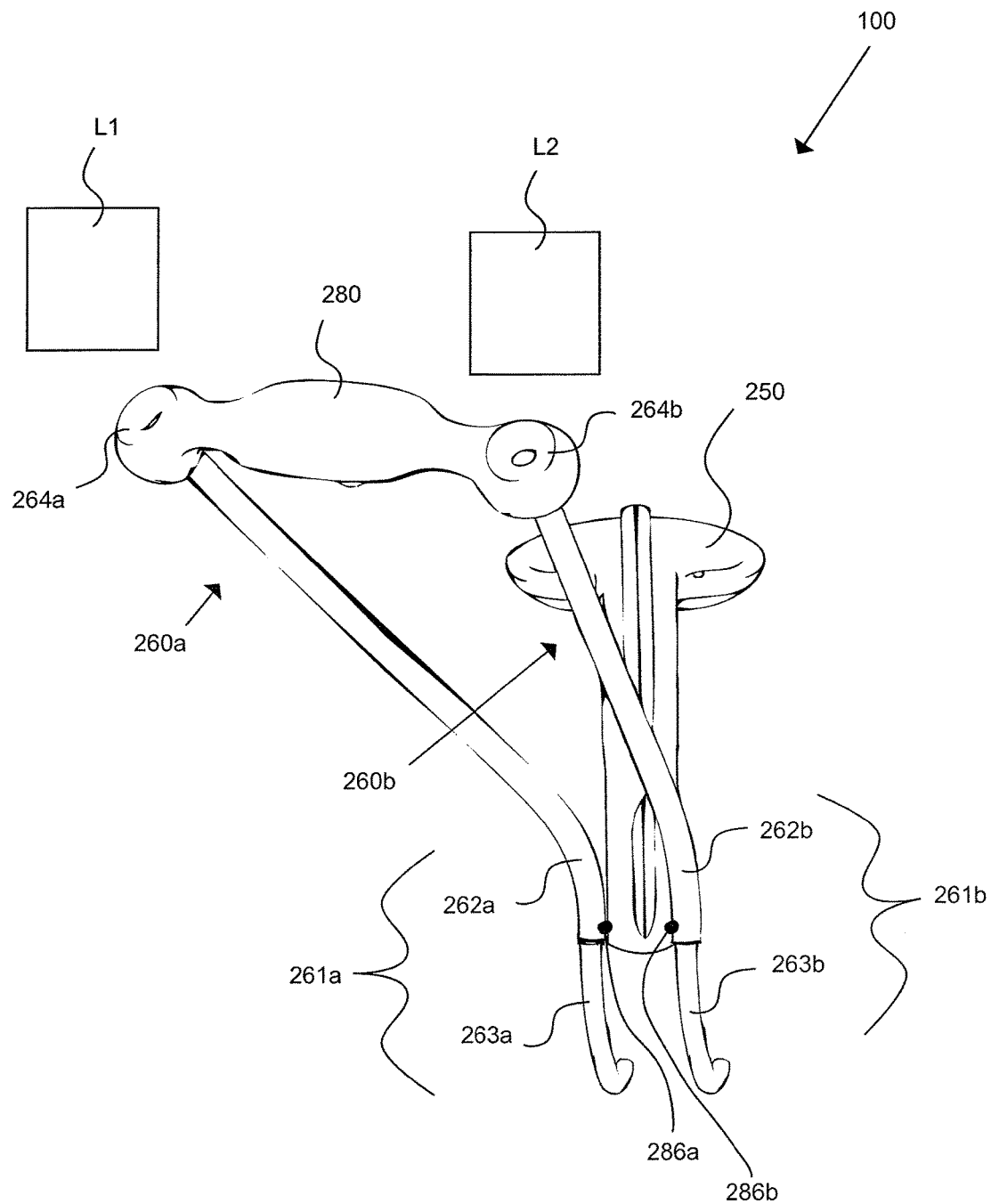
FIG. 3 is a perspective view of a tool positioning system, in accordance with an embodiment of the present inventive concepts.

The connector 280 comprises a first opening and a second opening, each constructed and arranged to operably engage a guide element of the first and second tool supports 260*a*, 260*b*. The first opening and the second opening can be constructed and arranged to position the first tool support 260*a* and the second tool support 260*b* in a non-parallel configuration. At least one of the first opening or the second opening can comprise a funnel-shaped opening, for example, for receiving a guide element 261, more specifically, a funnel-shaped proximal end 264 of an outer guide element 262 as shown in FIG. 3.

The tool positioning system 100 can include at least one fixation point, 133*a-e* shown (generally, 133), each constructed and arranged to attach to a stabilizing brace. A fixation point 133*a* can be positioned at the introduction device 250. A fixation point 133*b* can be positioned at the base 285. A fixation point 133*c* can be positioned at the first tool support 260*a*. A fixation point 133*d* can be positioned at the second tool support 260*b*. A fixation point 133*e* can be positioned at the connector 280. A brace 132, also referred to as a support, can be attached to the fixation point 133*a*. Another end of the brace 132 can be attached to other locations related to the tool positioning system 100, such as an operating room floor, the patient operating table (T) and/or an articulating probe feeder 110. The brace 132 can include a clamping device and the like for clamping to a floor table or other supporting object. Multiple braces can be coupled to different fixation points 133. For example, a brace (not shown) can be coupled between the fixation point 133*b* at the base 285 and a fixation point 133*c* at the first tool support 260*a*. Another brace 131 can be attached to the feeder 110 and can be clamped or otherwise attached to a floor, table or other object providing stability.

The system 100 can include a first human interface device (HID) 80*a* and a second HID 80*b* that communicate with a controller 85. As shown in FIG. 1, the first HID 80*a* can be proximate to or oriented toward the first operator location (L1) and the second HID 80*b* can be proximate to or oriented toward the second operator location (L2). In other embodiments, the first and second HIDs 80*a*, 80*b* can be part of a same hardware platform, and can be at a single or multiple operator location, for example, location (L1), and can permit an operator at either location L1 or L2 to access the HIDs 80*a*, 80*b* at the same location. Some or all of the first HID 80*a* and/or the second HID 80*b* can be integrated into a tool inserted at a tool support 260. In an embodiment, the system 100 includes a third HID 80*c* attached to integral with dogbone connector 280, HID 80*c* in wired or wireless communication with the controller 85.

Figure 6:
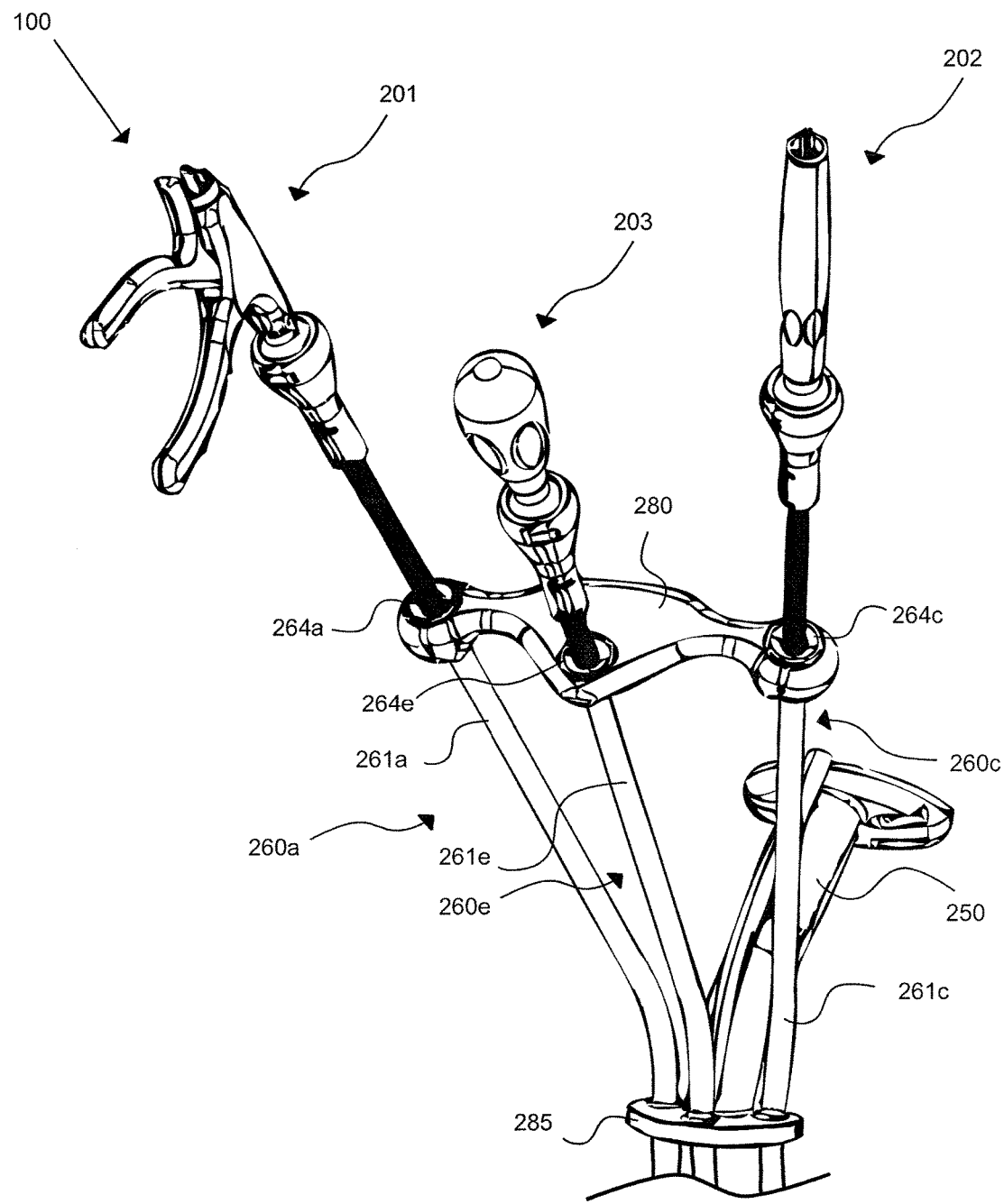
FIG. 6 is a perspective view of a tool positioning system having three tools in communication with a connector, in accordance with an embodiment of the present inventive concepts.

One or more HIDs 80*a*, *b*, *c* (generally, 80) can be constructed and arranged to manipulate the articulating probe 10, the tool supports 260, one or more tools inserted into tool supports 260, or a combination thereof. In system 100 of FIG. 1, the first HID 80*a* is oriented toward the first operator location (L1). The second HID 80*b* is oriented toward the second operator location (L2). A first operator, such as a medical professional, may control the articulating probe 10 via the HID 80*a* to steer, advance, retract or otherwise control the functions and movement of articulating probe 10 via commands sent to the controller 85. A light source, camera, or other device attached to the articulating probe may be activated in response to a control signal generated by the HID 80*a*. Alternatively or additionally, a second operator may control the articulating probe 10 via the second HID 80*b*, to steer, advance, retract or otherwise control the functions and movement of the articulating probe 10 via commands sent to the controller 85. A light source, camera, or other device attached to the articulating probe may be activated in response to a control signal generated by the HID 80*b*. The first HID 80*a* and/or the second HID 80*b* may include a device selected from the group consisting of: a haptic controller, a joystick, a track ball, a mouse and an electromechanical device. The articulating probe 10 may be controlled via an HID 80, and the surgical tools may be controlled via a tool handle, for example, a tool handle as shown in FIG. 6. One or more HIDs 80 can communicate with the controller by a physical connector, such as a conductive wire, or by a wireless connection, for example, a Bluetooth™ connection. An HID 80 can include switches, joystick, buttons, and the like for applying forces related to the movement of an articulating probe 10 shown in FIG. 4. In other embodiments, an HID 80 can include force sensors such as strain gauges, which can detect forces applied to a dogbone connector 280, for example, push, pull, and/or twist forces. Such forces can be applied for controlling the articulating probe 10 shown in FIG. 4, for example, to advance, retract, or steer the probe 10.

Figure 2:
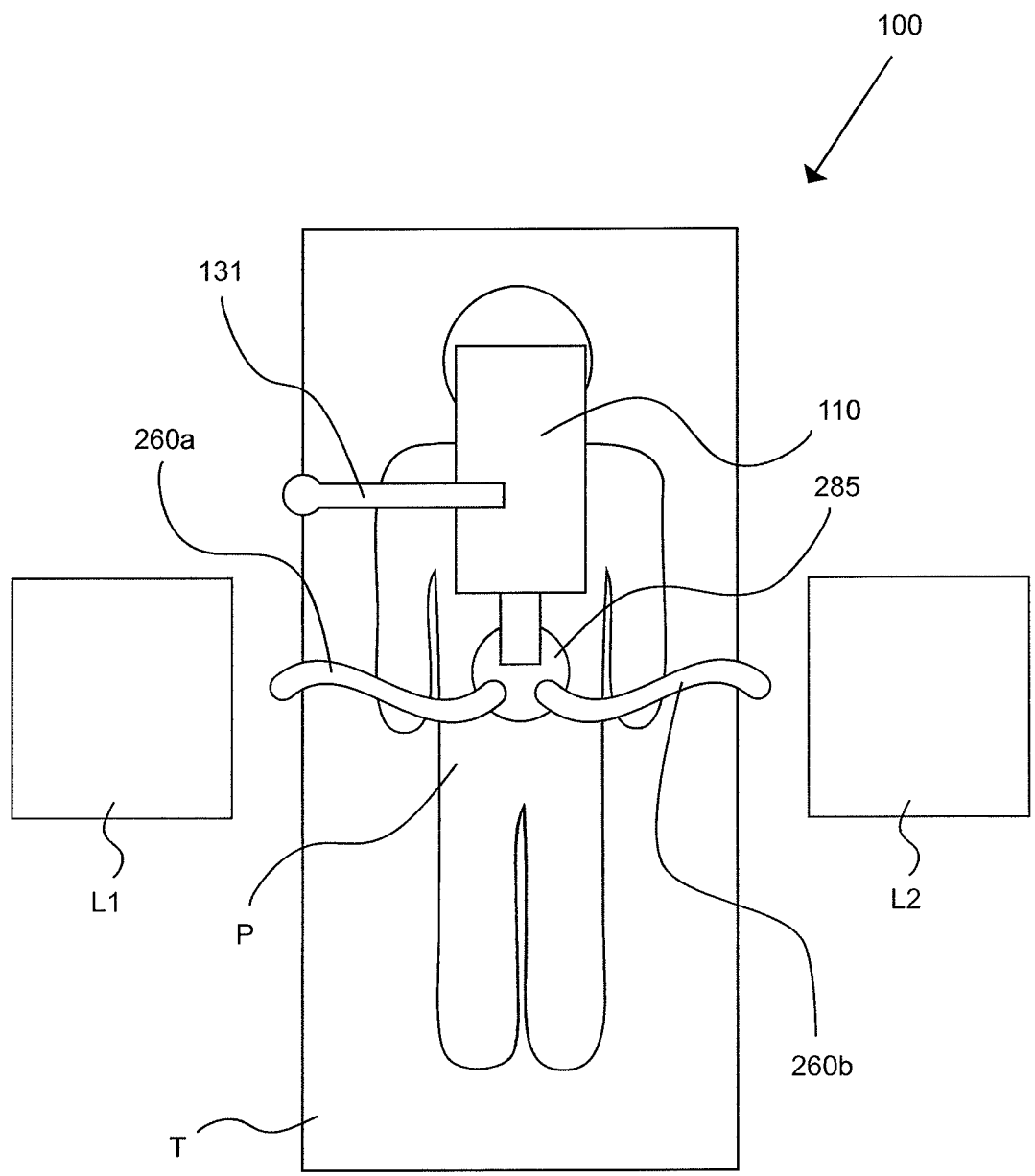
FIG. 2 is a top view of a tool positioning system for performing a medical procedure, in accordance with other embodiments of the present inventive concepts.

During a medical procedure, the patient (P) can lie on an operation table (T), for example, face up as shown in FIG. 1. In an embodiment, as shown in FIG. 1, the first operator location (L1) and second operator location (L2) can be side-by-side, or neighboring each other in a manner that permits two or more operators to each maneuver one or more tools. The first tool support 260*a* and/or the second tool support 260*b* can be constructed and arranged to provide tool access to a patient's head (H). For example, the first tool support 260*a* can provide tool access to a patient's esophagus via the patient's mouth. The first tool support 260*a* and/or the second tool support 260*b* can be constructed and arranged to provide tool access to at least one of a patient chest or a patient abdomen FIG. 2 is a top view of a tool positioning system 100 for performing a medical procedure, in accordance with other embodiments of the present inventive concepts. Many of the elements described with respect to FIG. 1 are the same as or similar to those of FIG. 2, and will therefore not be described again for brevity.

In the embodiment of FIG. 2, the first operator location (L1) and the second operator location (L2) are at face-to-face locations, for example, at opposite sides of an operating table (T) so that an operator at the first operator location (L1) and an operator at the second operator location (L2) can face each other. The first tool support 260a can extend in a direction towards the first operator location (L1) at a first side of the table (T) and the second tool support 260b can extend in a direction towards the second operator location (L2) at a second side of the table (T) opposite the first side. The first tool support 260a and/or the second tool support 260b can be constructed and arranged to provide tool access to a region of the patient's (P) body, for example, at least one of a patient chest or a patient abdomen.

As shown in FIG. 3, the first tool support 260a and the second tool support 260b can be fixedly coupled to a surface of the introduction device 250 instead of a base. In an embodiment, the first tool support 260a and/or the second tool support 260b are directly coupled to the introduction device 250 by attachment mechanisms, for example, welding points 286a, 286b, respectively. Alternatively, other bonding techniques, for example, adhesives and the like, can be applied. The connection at the introduction device 250 maintains a fixed distance and/or a fixed orientation between the first tool support 260a and the second tool support 260b. In some embodiments, the tool supports 260a and 260b can be rotatably attached to each other and/or a base for maintaining a fixed distance but not a fixed orientation. The first tool support 260a and the second tool support 260b can be fixed in position relative to each other. Accordingly, positions of the first and second tool supports 260a, 260b are maintained during an operation of the tool positioning system 100.

At least one of the first tool support 260a and the second tool support 260b can include first and second guide elements 261a, 261b, respectively. The first guide element 261a can include an outer guide element 262a, also referred to as a proximal guide element, and an inner guide element 263a, also referred to as a distal guide element. The second guide element 261b can include an outer guide element 262b and an inner guide element 263b. At least a portion of the inner guide element 263a, b (generally, 263) is flexible. The inner guide element 263 can be formed of plastic or related material. Materials can include but are not limited to fluoropolymers (e.g., polytetrafluoroethylene), fluorinated ethylene propylene, polyether block amide, high density polyethylene, low density polyethylene and/or nickel titanium alloy. Inner guide element 263 can comprise laser cut tubes (e.g. polymer or metal tubes) and/or coils or braids of plastic or metal. In some embodiments, inner guide element 263 comprises a polytetrafluoroethylene liner. In some embodiments, inner guide element 263 comprises a stainless steel coil. In some embodiments, inner guide element 263 comprises a coil covered by a polyether block amide. In some embodiments, inner guide element 263 comprises different varying stiffness along its length, such as when comprising a tube of varying durometers along its length. At least a portion of the outer guide element 262a, 262b (generally, 262) is rigid, with limited or no flexibility. As shown in FIG. 3, the outer guide elements 262a, 262b can be directly anchored to the introduction device 250 by a weld 286a, 286b, respectively.

The outer guide elements 262 can include a first tube. The inner guide elements 263 can include a second tube, a portion of which can be positioned in, and move relative to, the first tube of the outer guide element 262. In this manner, the inner guide element 263 can movably extend from the outer guide element 262, for example, in a telescoping configuration.

As shown in FIG. 4, a tool support 260 can rotatably engage the base 285. A single tool support 260 is shown in FIG. 4, however any tool support described herein (e.g. first tool support 260a, second tool support 260b, third tool support 260c, and/or fourth tool support 260d) can be configured as shown. The tool support 260 can be coupled to the base 285 by a gimbal 630, permitting the tool support 260 to rotate relative to the base 285, for example, allowing for three degrees of freedom between tool support 260 and base 285, which can include two-dimensional (X-Y) movement plus rotation. The gimbal 630 or other pivoted or ball and joint mechanism permits the guide element 261 of the tool support 260 to rotatably or fixedly engage the base 285, for example, at a mid-portion of the guide element 261. In embodiments where a tool support 260 is slidably adjustable, thus allowing for a shortening of a portion of the support 260 that attaches to the dogbone connector 280, the dogbone connector 280 may require adjustability of the distance between connector openings. Depending on the desired relative orientation of one support 260 to the other, parallel or angled, then the adjustability in the connector 280 for the distance between openings can occur along a straight or curved path. Alternatively, the guide element 261 of the tool support 260 can be fixedly attached to a base, for example, at a mid-portion of the guide element 261. The tool support 260 can be locked in a fixed position relative to the base 285. The system 100 can include a locking mechanism 635 to lock the at least one tool support 260 in the fixed position. The locking mechanism may be constructed to secure a position of the tool supports 260 with respect to the base 285, thus preventing the tool supports 260 from sliding or otherwise moving axially during movement of the tools by one or more operators.

The outer guide element 262 of the guide element 261 of a tool support 260 can be constructed and arranged to have a hollow elongate member. The hollow elongate member can be constructed and arranged as a structure known to those of ordinary skill in the art, for example, a hollow tube; a coil such as a helical coil, or combinations thereof. In an embodiment, the entire hollow elongate member is rigid. In another embodiment, at least a portion of the hollow elongate member can be rigid. The inner guide element 263 can be likewise constructed and arranged to have a hollow elongate member. In an embodiment, the entire hollow elongate member can include a flexible tube. Alternatively, the hollow elongate member can include at least a flexible portion. The inner guide element 263 can slide along an inner surface in the opening of the outer guide element 262 in which the inner guide element 263 is positioned.

The outer guide element 262 can have a funnel-shaped proximal end 264. The inner guide element 263 can likewise have a funnel shaped proximal end 265. Either or both funnels 264, 265 can be configured to readily and atraumatically introduce tools to the tool support 260. As shown in FIG. 3, a funnel shaped proximal end 264a, b of each tool support 260a, b, respectively, can be positioned about an opening in a connector 280.

The outer guide element 262 and/or inner guide element 263 can be constructed and arranged to guide or otherwise provide a support for a tool shaft so that it can be guided to a side port 637 coupled to an outer surface of the articulating probe 10.

The side port 637 can be coupled to a distal link 631 of the articulating probe 10. The side port 637 can be formed at a flange at the articulating probe 10. Multiple side ports may be positioned along the outer sleeve of the articulating probe 10 so as to provide a guide for one or more guide elements 261 that articulate in common with the articulating probe 10. Alternatively, the inner guide element 263 can be fixedly attached to the outer surface of the articulating probe 10, for example, the distal link 631, such as with an adhesive or mechanical fastener.

FIG. 5 is a perspective view of a tool positioning system 100 having multiple connectors 280, 280', in accordance with an embodiment.

The tool positioning system 100 can also comprise a first tool support 260a, a second tool support 260b, a third tool support 260c and a fourth tool support 260d. Each of tool supports 260a-d can include a funnel-shaped opening, 264a-d respectively, on its proximal end. The tool supports 260a-d and the introduction device 250 are fixedly attached to base 285. The third tool support 260c can comprise at least one guide element 261c, which can be similar to the guide elements 261a and 261b described herein. For example, the guide element 261c can include an outer guide element 262c and an inner guide element 263c. The fourth tool support 260d can comprise at least one guide element 261d, which can be similar to the guide elements 261a and 261b described herein. For example, the guide element 261d can include an outer guide element 262d and an inner guide element 263d.

The first tool support 260a and the third tool support 260c can be oriented in a same or similar direction, for example, toward a first operator location. The second tool support 260b and the fourth tool support 260d can be oriented in a same or similar direction, for example, toward a second operator location. Tools (not shown) extending from the first and third tool supports 260a, c, respectively, are shown positioned at a first side and a second side of a distal end of the articulating probe 10, and tools (not shown) extending from the second and fourth tool supports 260b, d, respectively, are shown positioned at the first side and the second side of the distal end of the articulating probe 10, where the first side is opposite the second side. In an alternative embodiment, not shown, tools extending from the first and third tool supports 260a, c, respectively, can be positioned at a first side of a distal end of the articulating probe 10, and tools extending from the second and fourth tool supports 260b, d, respectively, can be positioned at a second side of the distal end of the articulating probe 10.

The outer guide element 262a of the first tool support 260a and the outer guide element 262c of the third tool support 260c can be oriented in a same or similar direction, for example, toward a first operator location. The outer guide element 262b of the second tool support 260b and the outer guide element 262d of the fourth tool support 260d can be oriented in a same or similar direction, for example, toward a first operator location. However, the first and second inner guide elements 263a, b can be collocated, and the third and fourth inner guide elements 263c, d can be collocated.

The tool positioning system 100 can comprise a connector 280 attached to proximal ends of the first tool support 260a and the third tool support 260c. The connector 280 is constructed and arranged to maintain a relative position between the first tool support 260a and the third tool support 260c. The tool positioning system 100 can also comprise a second connector 280' attached to proximal ends of the second tool support 260b and the fourth tool support 260d. The connector 280' is constructed and arranged to maintain a relative position between the second tool support 260b and fourth tool support 260d. In another embodiment, the first connector 280 can be attached to proximal ends of the first tool support 260a and the second tool support 260b, and the second connector 280' can be attached proximal ends of the third tool support 260c and the fourth tool support 260d.

The connector 280, also referred to as a first connector or first dogbone connector, and/or the connector 280', also referred to as a second connector or second dogbone connector, can be removed from the tool supports 260 and replaced with a different connector 280", which can have different configuration parameters than the connectors 280, 280', for example, a different length or openings for receiving a funnel shaped guide element 261.

FIG. 6 is a perspective view of a tool positioning system 100 having three tools 201, 202, 203 in communication with a connector 280, in accordance with an embodiment. A single operator can operate tool positioning system 100, including any or all three tools 201, 202, 203. Alternatively, two or more operators can operate tool positioning system 100 of FIG. 6, including any or all three tools 201, 202, 203.

Three tool supports 260a, 260c, 260e extend between a base 285 and a connector 280. Each of tool supports 260a, 260c and 260e can include a funnel-shaped opening, 264a, 264c and 264e respectively, on their proximal end. The base 285 includes a collar having first, second, and third openings aligned with the first, second, and third tool supports 260a, 260c, 260e, respectively. The guide elements 261a, 261c, 261e (generally, 261) of the first, second, third and tool supports 260a, 260c, 260e, respectively, can extend through the first, second, and third openings so that mid-portions of the guide elements 261 are positioned in the openings during operation. The base 285 can include a fourth opening for receiving an introduction device 250.

At least one tool 201, 202, 203 can have a shaft, shown inserted into tool supports 260a, 260c and 260e, respectively, constructed and arranged to be slidingly received by a corresponding tool support 260. One or more tools 201, 202, 203 can be selected from the group consisting of: suction device; ventilator; light; camera; grasper; laser; cautery; clip applier; scissors; needle; needle driver; scalpel; RF energy delivery device; cryogenic energy delivery device; and combinations thereof. A tool 201, 202, 203 can include a rigid and/or a flexible tool shaft.

The connector 280 is attached to first, second, and third tool supports 260a, 260c, 260e and can be constructed and arranged to maintain a relative distance between the tool supports 260a, 260c, 260e. The connector 280 can be fixedly attached to one or more of the tool supports 260. Alternatively, the connector 280 can be rotatably attached to one or more of the tool supports 260. The connector 280 maintains a relative position of the third tool support 260e relative to the first tool support 260a and the second tool support 260c.

The base 285 can be fixedly attached to one or more of the tool supports 260. Alternatively, the base 285 can be rotatably attached to one or more of the tool supports 260. A gimbal (see FIG. 4) can be at the base 285 which rotatably engages one or more guide elements 261 at the base 285.

A single operator can operate one or more of: the tool 201 extending from the first tool support 260a, the tool 202 extending from the second tool support 260c, and/or the tool 203 extending from the third tool support 260e, for example, from a single operator location. Alternatively, one operator can operate two tools of the tools 201, 202, 203, and another operator can operate the remaining tool of the tools 201, 202, 203.

As shown in FIG. 7, a first tool 201 is positioned at a first side of a distal end of the articulating probe 10, i.e., the left side of the page as shown, and a second tool 202 is positioned at a second side of the distal end of the articulating probe 10, i.e., the right side of the page as shown, opposite the first side. A third tool 203 can optionally be positioned between the first and second tools 201, 202 at the distal end of the probe 10. First tool 201 has been inserted through a first tool support including inner guide element 263a. Inner guide element 263a passes through base 285, such as via a gimbal not shown but positioned behind probe 10. Second tool 202 has been inserted through a second tool support including inner guide element 263c. Inner guide element 263c passes through base 285 via gimbal 630c. Third tool 203 has been inserted through a third tool support including inner guide element 263e. Inner guide element 263e passes through base 285 via gimbal 630e. The first tool 201 can be controlled by an operator at the corresponding side of the articulating probe 10, i.e., the first side or left side of the page as shown. Alternatively, the first tool 201 can be controlled by an operator on the opposite side of the articulating probe 10, i.e., the second side or right side of the page as shown. The second tool 202 can be controlled by an operator at the corresponding side of the articulating probe 10, i.e., the second side or right side of the page as shown. Alternatively, the second tool 202 can be controlled by an operator on the opposite side of the articulating probe 10, i.e., the first side or left side of the page as shown. The operator at the first and second sides can be the same operator, or different operators at different locations, for example, side-by-side as shown in FIG. 1 or face-to-face as shown in FIG. 2.

As described above, the articulating probe 10 comprises a distal link 631, which can be positioned about an articulating probe 10. As shown in FIGS. 7 and 8A-D, the distal link 631 comprises at least three side ports 637. In FIG. 8B, the distal link 631" can include three side ports 637 that can be coupled to three tool supports, for example, tool supports 260a, c, e, respectively, shown in FIG. 6 and FIG. 7.

Figure 8A:
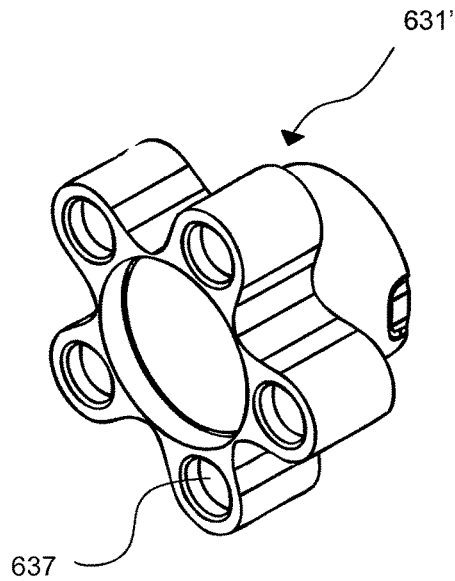
FIGS. 8A-8D are perspective views of distal links having multiple side ports, in accordance with an embodiment of the present inventive concepts.
Figure 8B:
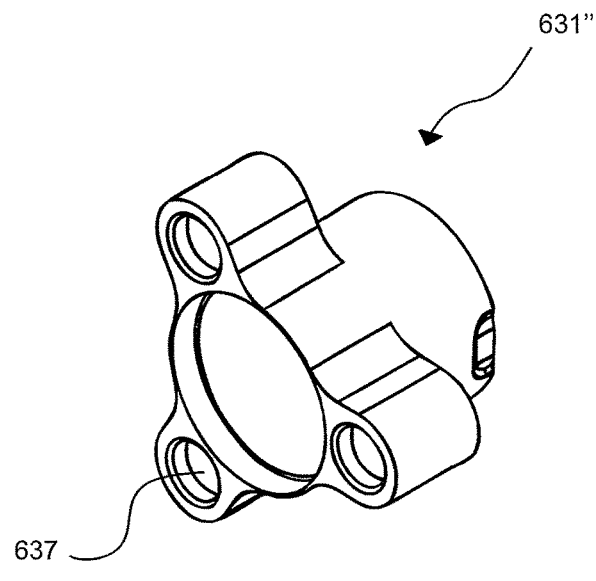
Figure 8C:
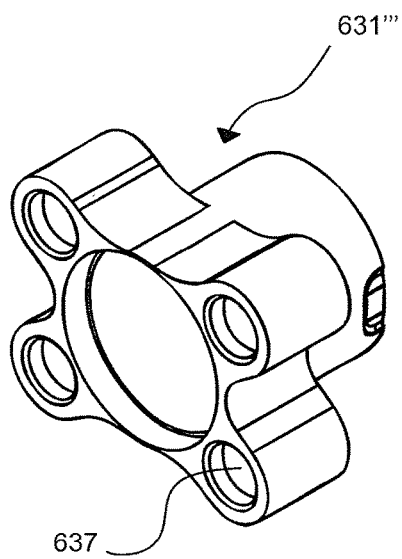

In another embodiment, as shown in FIG. 8C, a distal link 631''' comprises four side ports 637, which can be coupled to four tool supports, for example, tool supports 260a-d, respectively, shown in FIG. 5.

In another embodiment, as shown in FIG. 8A, a distal link 631' comprises five side ports 637, which can be coupled to five tool supports, for example, two tool supports oriented toward one operator location, and three tool supports oriented toward another operator location.

Figure 8D:
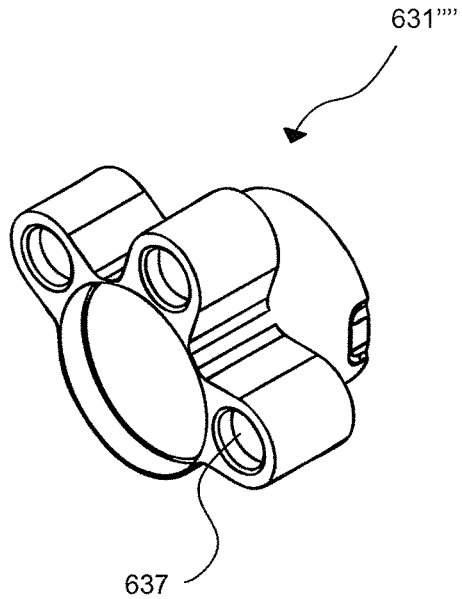

In an embodiment, as shown in FIG. 8B, the sideports 637 are symmetrically spaced about a periphery of the distal link 631". In an embodiment, as shown in FIG. 8D, the sideports 637 are asymmetrically spaced about a periphery of the distal link 631''''.

The side ports 637 can be positioned 30° to 180° apart from each other about a periphery of the connector 280. For example, as shown in FIG. 8D, first and second side ports 637 can be less than 180° apart from each other, such as 150° apart, and a third side port 637 can be positioned between the first and second side ports, such that the third side port 637 is less than 90° apart from each of the first and second side ports 637. The side ports 637 can be attached to one or more tool supports 260 oriented toward an operator location on a similar or dissimilar side as the side port 637.

While the present inventive concepts have been particularly shown and described above with reference to exemplary embodiments thereof, it will be understood by those of ordinary skill in the art, that various changes in form and detail can be made without departing from the spirit and scope of the present inventive concepts described and defined by the following claims.

What is claimed is:
1. A tool positioning system, comprising:
an introduction device constructed and arranged to slidingly receive an articulating probe;
a first tool support comprising at least one guide element constructed and arranged to slidingly receive a first tool, wherein the first tool support is oriented toward a first operator location; and
a second tool support comprising at least one guide element constructed and arranged to slidingly receive a second tool, wherein the second tool support is oriented toward a second operator location, the introduction device having a proximal region oriented away from the first and second tool supports and a distal region in communication with both the first and second tool supports.

2. The system of claim 1, wherein at least one of the first tool or the second tool is positioned at a patient to perform a medical procedure on the patient.

3. The system of claim 1, wherein at least one of the first tool support and the second tool support is directly anchored to the introduction device.

4. The system of claim 1 further comprising a base, wherein the first tool support and the second tool support are coupled to the base.

5. The system of claim 4, wherein the introduction device is coupled to the base and in communication with the first and second tool supports via the base.

6. The system of claim 5, wherein the base comprises a collar that surrounds at least a portion of the introduction device.

7. The system of claim 4, wherein at least one of the first tool support or the second tool support comprises at least one guide element that rotatably engages the base.

8. The system of claim 7, wherein the at least one of the first tool support and the second tool support comprises a gimbal which rotatably engages the at least one guide element at the base.

9. The system of claim 7, wherein the least one guide element of the first tool support comprises a mid-portion that rotatably engages the base.

10. The system of claim 7, wherein the at least one guide element of the first tool support is fixedly attached to the base.

11. The system of claim 4, wherein the first tool support rotatably engages the base and the second tool support rotatably engages the base.

12. The system of claim 4, wherein the at least one of the first or second tool supports moves linearly relative to the base.

13. The system of claim 1, wherein the system is constructed and arranged to slidingly receive two or more tools.

14. The system of claim 1, wherein the at least one guide element of the first tool support is constructed and arranged to receive a shaft of the first tool, and wherein the at least one guide element of the second tool support is constructed and arranged to receive a shaft of the second tool.

15. The system of claim 1, wherein the first tool is positioned at a first side of a distal end of the articulating probe and the second tool is positioned at a second side of the distal end of the articulating probe relatively opposite the first side.

16. The system of claim 15, wherein the first tool is controlled by an operator at the first operator location at the first side of the distal end of the articulating probe, and the second tool is controlled by an operator at the second operator location at the second side of the distal end of the articulating probe.

17. The system of claim 1, wherein the first tool and a third tool are positioned at a first side of a distal end of the articulating probe and the second tool and a fourth tool are positioned at a second side of the distal end of the articulating probe relatively opposite the first side.

18. The system of claim 17, wherein the first and third tools are controlled by an operator at the first operator location at the first side of the distal end of the articulating probe, and the second and fourth tools are controlled by an operator at the second operator location at the second side of the distal end of the articulating probe.

19. The system of claim 1, wherein at least one of the first tool support or the second tool support comprises a funnel shaped proximal end.

20. The system of claim 1, wherein at least one guide element of at least one of the first tool support or the second tool support comprises an inner guide element and an outer guide element.

21. The system of claim 20 wherein the outer guide element comprises a first tube and the inner guide element comprises a second tube slidingly positioned in the first tube.

22. The system of claim 20 wherein at least a portion of the inner guide element is flexible.

23. The system of claim 1 further comprising a third tool support, the third tool support comprising at least one guide element constructed and arranged to slidingly receive a third tool.

24. The system of claim 23, wherein the third tool support is oriented toward the first operator location.

25. The system of claim 23 further comprising a connector coupled to the first tool support and the third tool support, wherein the connector is constructed and arranged to maintain a relative position between the first tool support and the third tool support.

26. The system of claim 23 further comprising a fourth tool support, the fourth tool support comprising at least one guide element constructed and arranged to slidingly receive a fourth tool.

27. The system of claim 26, wherein the fourth tool support is oriented toward the second operator location.

28. The system of claim 26 further comprising a connector coupled to the second tool support and the fourth tool support, wherein the connector is constructed and arranged to maintain a relative position between the second tool support and the fourth tool support.

29. The system of claim 26 further comprising a connector coupled to a proximal end of each of the first and third tool supports, and a connector attached to a proximal end of each of the second and fourth tool supports.

30. The system of claim 1 further comprising a connector coupled to the first tool support and the second tool support, wherein the connector is constructed and arranged to maintain a relative position between the first tool support and second tool support.

31. The system of claim 30, wherein the connector is rotatably coupled to at least one of the first or the second tool support.

32. The system of claim 1 further comprising a third tool support and a connector coupled to the first, second and third tool supports, wherein the connector is constructed and arranged to maintain a relative position between the first, second, and third tool supports.

33. The system of claim 1 wherein the at least one guide element of the first tool support or the second tool support comprises a hollow elongate member.

34. The system of claim 1, wherein the first operator location and the second operator location comprise side-by-side locations.

35. The system of claim 1, wherein the first operator location and the second operator location comprise face-to-face locations.

36. The system of claim 1 further comprising a fixation point constructed and arranged to attach to a stabilizing brace.

37. The system of claim 36 further comprising a connector coupled to the first tool support and the second tool support, wherein the connector is constructed and arranged to maintain a relative position between the first tool support and second tool support, and wherein the connector comprises the fixation point.

38. The system of claim 36, wherein the introduction device comprises the fixation point.

39. The system of claim 36 further comprising a base coupling the first tool support and the second tool support, wherein the base comprises the fixation point.

40. The system of claim 36 further comprising a brace attachable to the fixation point.

41. The system of claim 36 further comprising a second fixation point constructed and arranged to attach to a stabilizing brace.

42. The system of claim 41 further comprising a first brace for attachment to the first fixation point and a second brace for attachment to the second fixation point.

43. The system of claim 1 further comprising at least one tool constructed and arranged to be slidingly received by at least one of the first tool support or the second tool support.

44. The system of claim 43, wherein the at least one tool comprises at least two tools, wherein each tool comprises a shaft constructed and arranged to be slidingly received by at least one of the first tool support or the second tool support.

45. The system of claim 43, wherein the at least one tool comprises a tool selected from the group consisting of: a suction device, a ventilator, a light, a camera, a grasper, a laser, a cautery, a clip applier, a scissors, a needle, a needle driver, a scalpel, an RF energy delivery device, a cryogenic energy delivery device, and combinations thereof.

46. A tool positioning system, comprising:
   an articulating probe;
   an introduction device constructed and arranged to slidingly receive the articulating probe;
   a first tool support comprising at least one guide element constructed and arranged to slidingly receive a first tool, wherein the first tool support is oriented toward a first operator location; and
   a second tool support comprising at least one guide element constructed and arranged to slidingly receive a second tool, wherein the second tool support is oriented toward a second operator location, the introduction device having a proximal region oriented away from the first and second tool supports and a distal region in communication with both the first and second tool supports.

47. The system of claim 46, wherein the articulating probe comprises a distal link.

48. The system of claim 47, wherein the distal link comprises at least a first sideport coupled to the first tool support and a second sideport coupled to the second tool support.

49. The system of claim 47, further comprising a third tool support wherein the distal link comprises at least a first sideport coupled to the first tool support, a second sideport coupled to the second tool support and a third sideport coupled to the third tool support.

50. The system of claim 46 further comprising a controller constructed and arranged to manipulate the articulating probe.

51. The system of claim 50 further comprising a first human interface device oriented toward the first operator location, the first human interface generating a first control signal received by the controller for manipulating the articulating probe.

52. A tool positioning system, comprising:
- a first tool support comprising at least one guide element constructed and arranged to slidingly receive a first tool, wherein the first tool support is oriented toward a first operator location;
- a second tool support comprising at least one guide element constructed and arranged to slidingly receive a second tool, wherein the second tool support is oriented toward a second operator location; and
- a base that couples the first tool support and the second tool support, the base including a collar that surrounds at least a portion of the introduction device, that extends in a lateral direction relative to a direction of extension of the introduction device, and that has first and second openings for receiving the first and second tool supports, respectively.

* * * * *